US006528060B1

(12) United States Patent
Nicolette

(10) Patent No.: US 6,528,060 B1
(45) Date of Patent: Mar. 4, 2003

(54) THERAPEUTIC COMPOUNDS

(75) Inventor: Charles A. Nicolette, Framingham, MA (US)

(73) Assignee: Genzyme Corporation, Framingham, MA (US)

( * ) Notice: Subject to any disclaimer, the term of this patent is extended or adjusted under 35 U.S.C. 154(b) by 0 days.

(21) Appl. No.: 09/527,487

(22) Filed: Mar. 16, 2000

(51) Int. Cl.[7] ......................... A61K 39/00; A61K 38/04

(52) U.S. Cl. .................................... 424/185.1; 530/328

(58) Field of Search ........................ 424/185.1; 530/328

(56) References Cited

U.S. PATENT DOCUMENTS

| | | | |
|---|---|---|---|
| 4,683,195 A | | 7/1987 | Mullis et al. |
| 4,683,202 A | | 7/1987 | Mullis |
| 4,754,065 A | | 6/1988 | Levenson et al. |
| 4,800,159 A | | 1/1989 | Mullis et al. |
| 5,440,013 A | | 8/1995 | Kahn |
| 5,837,249 A | | 11/1998 | Heber-Katz et al. |
| 5,869,445 A | * | 2/1999 | Cheever et al. |

FOREIGN PATENT DOCUMENTS

| | | |
|---|---|---|
| WO | WO 96/23060 | 8/1996 |

OTHER PUBLICATIONS

Stryer et al., Biochemistry, W.H. Freeman and Company. New York, pp. 18–22, 1988.*

Fisk et al ., Immunol 18(4): 197–209; 1996.*

Parker et al., Immunol Res 14: 34–57; 1995.*

Rongeun, Yang, et al., "Identification of New HER2/neu–Derived Peptide Epitopes That Can Elicit Specific CTL Aganist Autologous and Allogenic Carcinomas and Melanomas" (1999) *J. Immunol* 163: 1037–1044.

Altman, J.D. et al., "Phenotypic analysis of antigen–specific T lymphocytes" (1996) *Science* 274(5284):94–96.

Bertoni, R. et al., "Human class I supertypes and CTL repertoires extend to chimpanzees" (1998) *J. Immunol.* 161:4447–4455.

Boczkowski, D. et al., "Dendritic cells pulsed with RNA are potent antigen–presenting cells in vitro and in vivo" (1996) *J. Exp. Med.* 184:465–472.

Bordignon, C. et al., "Retroviral vector–mediated high–efficiency expression of adenosine deaminase (ADA) in hematopoietic long–term cultures of ADA–deficient marrow cells" (1989) *PNAS USA* 86:6748–6752.

Carter, B.J., "Adeno–associated virus vectors" (1992) *Curr. Op. Biotechnol.* 3:533–539.

Caruso, A. et al., "Flow cytometric analysis of activation markers on stimulated T cells and their correlation with cell proliferation" (1997) *Cytometry* 27:71–76.

Correll, P.H. et al., "Production of human glucocerebrosidase in mice after retroviral gene transfer into multipotential hematopoietic progenitor cells" (1989) *PNAS USA* 86:8912–8916.

Coulie, P.G., "Human tumour antigens recognized by T cells: new perspectives for anti–cancer vaccines?" (1997) *Molec. Med. Today* 3:261–268.

Culver, K. et. al., "Lymphocytes as cellular vehicles for gene therapy in mouse and man" (1991) *PNAS USA* 88:3155–3159.

Dharanipragada, R. et al., "The absolute configuration of an intermediate in the asymmetric synthesis of unusual amino acids" (1992) *Acta. Cryst.* C48:1239–1241.

Dharanipragada, R. et al., "Synthetic linear and cyclic glucagon antagonists" (1993) *Int. J. Peptide Protein Res.* 42(1):68–77.

DiMaio, J. et al., "Synthesis of chiral piperazin–2–ones as model peptidomimetics" (1989) *J. Chem. Soc. Perkin Trans.* 1(9):1687–1689.

Feltkamp, M.C.W. et al., "Competition inhibition of cytotoxic T–lymphocyte (CTL) lysis, a more sensitive method to identify candidate CTL epitopes than induction of antibody–detected MHC class I stabilization" (1995) *Immunol. Lett*, 47:1–8.

Ferguson, et al. "Cell–surface anchoring of proteins via glycosyl–phosphatidylinositol structures" (1988) *Ann. Rev. Biochem.* 57:285–320.

Fujihashi, K. et al., "Cytokine–specific ELISPOT assay single cell analysis of IL–2, IL–4 and IL–6 producing cells" (1993) *J. Immunol. Meth.* 160:181–189.

Garvey D.S. et al., "3,4–disubstituted γ–lactam rings as conformationally constrained mimics of peptide derivatives containing aspartic acid or norleucine" (1990) *J. Org. Chem.* 55(3):936–940.

Hruby, V.J., "Conformational restrictions of biologically active peptides via amino acid side chain groups" (1982) *Life Sciences* 31:189–199.

Hruby, V.J. et al. "Emerging approaches in the molecular design of receptor–selective peptide ligands: conformational, topographical and dynamic considerations" (1990) *Biochem J.* 268:249–262.

Isakov, N. et al., "ZAP–70 binding specificity to T cell receptor tyrosine–based activation motifs: The tandem SH2 domains of ZAP–70 bind distinct tyrosine–based activation motifs with varying affinity" (1995) *J. Exp. Med.* 181:375–380.

Jones, R.C.F. and G.J. Ward, "Amide bond isosteres: imidazolines in pseudopeptide chemistry" (1988) *Tetrahedron Lett.* 29(31)3853–3856.

(List continued on next page.)

*Primary Examiner*—Christina Chan
*Assistant Examiner*—Phuong D. Huynh
(74) *Attorney, Agent, or Firm*—Bingham McCutchen LLP; Antoinette F. Konski

(57) ABSTRACT

The present invention provides synthetic compounds, antibodies that recognize and bind to these compounds, polynucleotides that encode the compounds, and immune effector cells raised in response to the presentation of these compounds. The invention further provides methods for inducing an immune response and administering immunotherapy to a subject by delivering the compounds of the invention.

2 Claims, No Drawings-

OTHER PUBLICATIONS

Kahn, M. and S. Bertenshaw, "The incorporation of γ–turn prosthetic units into merrifield solid phase peptide synthesis" (1989) *Tetrahedron Lett.* 30(18):2317–2320.

Karlsson, S. et al., "Stable gene transfer and tissue–specific expression of a human globin gene using adenoviral vectors" (1986) *The EMBO J.* 5(9):2377–2385.

Kawakami, Y. et al., "Cloning of the gene coding for a shared human melanoma antigen recognized by autologous T cells infiltrating into tumor" (1994) *PNAS USA* 91(9):3515–3519.

Kazmierski, W. M. and V.J. Hruby, "Asymmetric synthesis of topographically constrained amino acids: synthisis of the optically pure isomers of α,γ–dimethyl–phenylalanine and α,β–dimethyl–1,2,3,4–tetrahydroisoquinoline–3–carboxylic acid" (1991) *Tetrahedron Lett.* 32(41):5769–5772.

Kazmierski, W.M. et al., "Topographic design of peptide neurotransmitters and hormones on stable backbone templates: relation of conformation and dynamics to bioactivity" (1991) *J. Am. Chem. Soc.* 113:2275–2283.

Kemp, D.S. and P.E. McNamara, "Conformationally restricted cyclic nonapeptides derived from L–cysteine and LL–3–amino–2–piperidone–6–carboxylic acid (LL–Acp), a potent γ–turn–inducing dipeptide analogue" (1985) *J. Org. Chem.* 50:5834–5838.

Kemp, D.S. and B.R. Bowen, "Conformational analysis of peptide–functionalized diacylaminoepindolidiones $^1$H NMR evidence for γ–sheet formation" (1988) *Tetrahedron Lett.* 29(40):5081–5082.

Kemp, D.S. and W.E. Stites, "A convenient preparation of derivatives of 3(S)–amino–10(R)–carboxy–1, 6–diaza–cyclodeca–2, 7–dione The dilactam of L–α, γ–diaminobutyric acid and D–glutamic acid: A β–turn template" (1988) *Tetrahedron Lett.* 29(40):5057–5060.

Kemp, D.S. and T.P. Curran, "(2, 5S, 8S, 11S)–1–acetyl–1, 4–diaza–3–keto–5–carboxy–10–thia–tricyclo–[2.8.0 $^{4,8}$]–ridecane, 1 the preferred conformation of 1 (1=αtemp–OH) and its peptide conjugates αtemp–L–(Ala)$_n$–OR (n=1 to 4) and α–temp –L–Ala–L–Phe–Lys(εBoc)–L–Lys(ε–Boc)–NHMe studies of templates for α–helix formation" (1988) *Tetrahedron Lett.* 29(39):4935–4938.

Kemp, D.S. and J.S. Carter, "Amino acid derivatives that stabilize secondary structures of polypeptides. 4. Practical synthesis of 4–(alkylamino)–3–cyano–6–azabicyclo[3.2.1] oct–3–enes (ben derivatives)as γ–turn templates" (1989) *J. Org. Chem.* 54:109–115.

McGrory, W.J. et al., "Short communications: A simple technique for the rescue of early region I mutation into infectious human adenovirus type 5" (1988) *Virology* 163:614–617.

Merrifield, R.B., "New approaches to the chemical synthesis of peptides" (1967) *Recent Progress in Hormone Res.* 23:451–482.

Miyake, A. et al., "Synthesis and angiotensin converting enzyme inhibitory activity of 1,2,3,4–tetrahydroisoquinoline–3–carboxylic acid derivatives" (1984) *J. Takeda Res. Labs.* 43(3/4):53–76.

Mosier, D.E. et al., "Resistance to human immunodeficiency virus 1 infection of SCID mice reconstituted with peripheral blood leukocytes from donors vaccinated with vaccinia gp160 and recombinant gp160" (1993) *PNAS. USA* 90:2443–2447.

Muzcyzka, "Use of adeno–associated virus as a general transduction vector for mammalian cells" (1992) *Curr. Top. Microbiol. Immunol.* 158:97–129.

Nagai, U. and K. Sato, "Synthesis of a bicyclic dipeptide with the shape of γ–turn central part" (1985) *Tetrahedron Lett.* 26(5):647–650.

Nair, S.et al., "Soluble proteins delivered to dendritic cells via pH–sensitive liposomes induce primary cytotoxic T lymphocyte responses in vitro" (1992) *J. Exp. Med.* 175:609–612.

Olson, G.L. et al., "Design and synthesis of a protein γ–turn mimetic" (1990) *J. Am. Chem. Soc.* 112:323–333.

Paglia, P. et al., "Murine dendritic cells loaded in vitro with soluble protein prime cytotoxic T lymphocytes against tumor antigen in vivo" (1996) *J. Exp. Med.* 183:317–322.

Pardoll, D.M., "Cancer vaccines" (1998) *Nature Med.* 4(5 Suppl.):525–531.

Parker, et al., "Sequence motifs important for peptide binding to the human MHC class I molecule, HLA–A2" (1992) *J. Immunol.* 149(11):3580–3587.

Parker, K.C. et al. (1995) "Peptide Birding to MCH Class 1 Molecules: Implications for Antigenic Peptide Prediction" *Immunol. Res.* 14:34–57.

Parkhurst, M.R. et al., "Improved induction of melanoma–reactive CTL with peptides from the melanoma antigen gp100 modified at HLA–A*0201–binding residues" (1996) *J. Immunol.* 157:2539–2548.

al–Ramadi, B.K. et al., "Lack of strict correlation of functional sensitization with the apparent affinity of MHC/peptide complexes for the TCR" (1992) *J. Immunol.* 155(2):662–673.

Rill, D.R. et al., "An approach for the analysis of relapse and marrow reconstitution after autologous marrow transplantation using retrovirus–mediated gene transfer" (1992) *Blood* 79(10):2694–2700.

Rouse, R.J.D. et al., "Induction in vitro of primary cytotoxic T–lymphocyte responses with DNA encoding herpes simplex virus proteins" (1994) *J. Virol.* 68(9):5685–5689.

Salazar, E. et al., "Agonist peptide from a cytotoxic T–lymphocyte epitope of human carcinoembryonic antigen stimulates production of TC1–type cytokines and increases tyrosine phosphorylation more efficiently than cognate peptide" (2000) *Int. J. Cancer* 85:829–838.

Samanen, J. et al., "5,5–dimethylthiazolidine–4–carboxylic acid (DTC) as a proline analog with restricted conformation" (1990) *Int. J. Peptide Protein Res.* 35:501–509.

Schlesinger, S. and T.W. Dubensky, Jr., "Alphavirus vectors for gene expression and vaccines" (1999) *Curr Opin Biotechnol.* 10(5):434–439.

Sette, A. et al., "The relationship between class I binding affinity and immunogenicity of potential cytotoxic T cell epitopes" (1994) *J. Immunol.* 153(12):5586–5592.

Shirai, M. et al., "CTL responses of HLA–A2.1–transgenic mice specific for hepatitis C viral peptides predict epitopes for CTL of humans carrying HLA–A2.1" (1995) *J. Immunol.* 154:2733–2742.

Stuber, G. et al., "HLA–A0201 and HLA–B7 binding peptides in the EBV–encoded EBNA–1, EBNA–2 and BZLF–1 proteins detected in the MHC class 1 stabilization assay. Low proportion of binding motifs for several HLA class 1 alleles in EBNA–1" (1995) *Int. Immunol.* 7(4):653–663.

Tan, L. et al., "An improved assembly assay for peptide binding to HLA–B*2705 and H–2K*class I MHC molecules" (1997) *J. Immunol. Meth.* 209(1):25–36.

Tanguay, S. and J.J. Killion, "Direct comparison of ELISPOT and ELISA–based assays for detection of individual cytokine–secreting cells" (1994) *Lymphokine Cytokine Res.* 13(4):259–263.

Valmori, D. et al., "Induction of potent antitumor CTL responses by recombinant vaccinia encoding a melan–A peptide analogue" (2000) *J. Immunol.* 164(2):1125–1131.

van der Burg, S.H. et al., "Immunogenicity of peptides bound to MHC class I molecules depends on the MHC–peptide complex stability" (1996) *J. Immunol.* 156:3308–3314.

Ware, C.F. et al., "Recognition of HLA–A2 mutant and variant target cells by an HLA–A2 allospecific human cytotoxic T lymphocyte line" (1983) *J. Immunol.* 131(3):1312–1317.

Wilchek, M. and E.A. Bayer, "The avidin–biotin complex in bioanalytical applications" (1988) *Anal. Biochem.* 171:1–32.

Ying, H. et al., "Cancer therapy using a self–replicating RNA vaccine" (1999) *Nat. Med.* 5(7):823–827.

Zabrocki, J.et al., "Conformational mimicry. 1. 1,5–disubstituted tetrazole ring as a surrogate for the cis amide bond" (1988) *J. Am. Chem. Sci.* 110:5875–5880.

Zechel, C. et al., "Synthetic glucagon antagonists and partial agonists" (1991) *Int. J. Pep. Protein Res.* 38(2):131–138.

Zuegel, et al., "Termination of peripheral tolerance to a T cell epitope by heteroclitic antigen analogues" (1998) *J. Immunol.* 161(4):1705–1709.

Zweerink, H.J. et al., "Presentation of endogenous peptides to MHC class I–restricted cytotoxic T lymphocytes in transport deletion mutant T2 cells" (1993) *J. Immunol.* 150(5):1763–1771.

* cited by examiner

THERAPEUTIC COMPOUNDS

TECHNICAL FIELD

The invention relates to the field of therapeutic antigenic compounds that are useful to modulate an antigen-specific immune response.

BACKGROUND OF THE INVENTION

The recognition of antigenic epitopes presented by molecules of the Major Histocompatibility Complex (MHC) plays a central role in the establishment, maintenance and execution of mammalian immune responses. T cell surveillance and recognition of peptide antigens presented by cell surface MHC molecules expressed by somatic cells and antigen presenting leukocytes functions to control invasion by infectious organisms such as viruses, bacteria, and parasites. In addition it has now been demonstrated that antigen specific cytotoxic T lymphocytes (CTL's) can recognize certain cancer cell antigens and attack cells expressing these antigens. This T cell activity provides a basis for developing novel strategies for anti-cancer vaccines. Furthermore, inappropriate T cell activation plays a central role in a certain debilitating autoimmune diseases such as rheumatoid arthritis, multiple sclerosis, and asthma. Thus presentation and recognition of antigenic epitopes presented by MHC molecules plays a central role in mediating immune responses in multiple pathological conditions.

The ability of a particular peptide to function as a T cell epitope requires that it bind effectively to the antigen presenting domain of an MHC molecule and also that it display an appropriate set of amino acids that can be specifically recognized by a T cell receptor molecule. While it is possible to identify natural T cell epitopes derived from antigenic polypeptides, these peptide epitopes do not necessarily represent antigens that are optimized for inducing a particular immune response. In fact, it has been shown that it is possible to improve the effectiveness of natural epitopes by introducing single N multiple amino acids substitutions that alter their sequence (Valmori et al., 2000. J. Immunol 164(2): 1125–1131). Thus, delivery of carefully optimized synthetic peptide epitopes has the potential to provide an improved method to induce a useful immune response.

The introduction into an animal of an antigen has been widely used for the purposes of modulating the immune response, or lack thereof, to the antigen for a variety of purposes. These include vaccination against pathogens, induction of an immune response to a cancerous cell, reduction of an allergic response, reduction of an immune response to a self antigen that occurs as a result of an autoimmune disorder, reduction of allograft rejection, and induction of an immune response to a self antigen for the purpose of contraception.

Enhancement of the speed and affinity of an immune response to a foreign antigen is the basis of vaccination protocols in which a killed, or live attenuated pathogen, or an antigenic part of a pathogen, is introduced into an individual. One significant disadvantage of such vaccines is that they pose an inherent threat that the virus is not sufficiently attenuated or killed. There is thus the potential for the vaccine to cause the disease against which protection is sought.

In the treatment of cancer, a variety of immunotherapeutic approaches have been taken to generate populations of cytotoxic T lymphocytes which specifically recognize and lyse tumor cells. Many of these approaches depend in part on identifying and characterizing tumor-specific antigens.

More recently, certain pathogen- and tumor-related proteins have been immunologically mimicked with synthetic peptides whose amino acid sequence corresponds to that of an antigenic determinant domain of the pathogen- or tumor-related protein. Despite these advances, peptide immunogens based on native sequences generally perform less than optimally with respect to inducing an immune response. Thus, a need exists for modified synthetic antigenic peptide epitopes with enhanced immunomodulatory properties. This invention satisfies this need and provides related advantages as well.

DISCLOSURE OF THE INVENTION

The present invention provides novel, synthetic compounds that are useful in a variety of methods of modulating an immune response to the synthetic and naturally occurring compounds.

Further provided are polynucleotides encoding the therapeutic compounds, gene delivery vehicles comprising these polynucleotides and host cells comprising these polynucleotides.

In addition, the invention provides methods for inducing an immune response in a subject comprising delivering the compositions of the invention, and delivering the peptide compositions of the invention in the context of an MHC molecule.

The peptides of the invention are useful to generate antibodies that specifically recognize and bind to these molecules. These antibodies are further useful for immunotherapy when administered to a subject.

The invention also provides immune effector cells raised in the presence and at the expense of an antigen presenting cell that presents the peptide compositions of the invention in the context of an MHC molecule and a method of adoptive immunotherapy comprising administering an effective amount of these immune effector cells to a subject.

DESCRIPTION OF THE SEQUENCE LISTINGS

SEQ ID NO:1. The complete nucleotide sequence of a cDNA encoding the human tyrosine kinase-type receptor HER2. The coding region extends from position 151 through position 3918.

SEQ ID NO:2. The amino acid sequence of the native human tyrosine kinase-type receptor HER2. The compounds of the invention are variations based on native HER2 peptide 774–782.

SEQ ID NO:3. The amino acid sequence of compound 1 (FLYYGTTYV).

SEQ ID NO:4. The polynucleotide sequence encoding compound 1.

SEQ ID NO:5. The amino acid sequence of compound 2 (FLFTPTIYV).

SEQ ID NO:6. The polynucleotide sequence encoding compound 2.

SEQ ID NO:7. The amino acid sequence of compound 3 (FLFDPTTYV).

SEQ ID NO:8. The polynucleotide sequence encoding compound 3.

MODES OF CARRYING OUT THE INVENTION

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

The practice of the present invention employs, unless otherwise indicated, conventional techniques of molecular biology (including recombinant techniques), microbiology, cell biology, biochemistry and immunology, which are within the skill of the art. Such techniques are explained fully in the literature. These methods are described in the following publications. See, e.g., Sambrook et al. MOLECULAR CLONING: A LABORATORY MANUAL, $2^{nd}$ edition (1989); CURRENT PROTOCOLS IN MOLECULAR BIOLOGY (F. M. Ausubel et al. eds. (1987)); the series METHODS IN ENZYMOLOGY (Academic Press, Inc.); "PCR: A PRACTICAL APPROACH" (M. MacPherson et al. IRL Press at Oxford University Press (1991)); PCR 2: A PRACTICAL APPROACH (M. J. MacPherson et al., eds. (1995)); ANTIBODIES, A LABORATORY MANUAL (Harlow and Lane eds. (1988)); and ANIMAL CELL CULTURE (R. I. Freshney ed. (1987)).

Definitions

As used herein, certain terms may have the following defined meanings.

As used in the specification and claims, the singular form "a," "an" and "the" include plural references unless the context clearly dictates otherwise. For example, the term "a cell" includes a plurality of cells, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

A "native" or "natural" antigen is a polypeptide, protein or a fragment which contains an epitope, which has been isolated from a natural biological source, and which can specifically bind to an antigen receptor, in particular a T cell antigen receptor (TCR), in a subject.

The term "antigen" is well understood in the art and includes substances which are immunogenic, i.e., immunogens, as well as substances which induce immunological unresponsiveness, or anergy, i.e., anergens.

An "altered antigen" is one having a primary sequence that is different from that of the corresponding wild-type antigen. Altered antigens can be made by synthetic or recombinant methods and include, but are not limited to, antigenic peptides that are differentially modified during or after translation, e.g., by phosphorylation, glycosylation, cross-linking, acylation, proteolytic cleavage, linkage to an antibody molecule, membrane molecule or other ligand. (Ferguson et al. (1988) Ann. Rev. Biochem. 57:285–320). A synthetic or altered antigen of the invention is intended to bind to the same TCR as the natural epitope.

A "self-antigen" also referred to herein as a native or wild-type antigen is an antigenic peptide that induces little or no immune response in the subject due to self-tolerance to the antigen. An example of a self-antigen is the human growth factor receptor HER2.

The term "tumor associated antigen" or "TAA" refers to an antigen that is associated with or specific to a tumor. Examples of known TAAs include gp100, MART and MAGE.

The terms "major histocompatibility complex" or "MHC" refers to a complex of genes encoding cell-surface molecules that are required for antigen presentation to T cells and for rapid graft rejection. In humans, the MHC complex is also known as the HLA complex. The proteins encoded by the MHC complex are known as "MHC molecules" and are classified into class I and class II MHC molecules. Class I MHC include membrane heterodimeric proteins made up of an a chain encoded in the MHC noncovalently linked with the β2-microglobulin. Class I MHC molecules are expressed by nearly all nucleated cells and have been shown to function in antigen presentation to CD8+T cells. Class I molecules include HLA-A, B, and C in humans. Class II MHC molecules also include membrane heterodimeric proteins consisting of noncovalently associated α and β chains. Class II MHC molecules are known to function in CD4+T cells and, in humans, include HLA-DP, -DQ, and DR.

The term "antigen-presenting matrix", as used herein, intends a molecule or molecules which can present antigen in such a way that the antigen can be bound by a T-cell antigen receptor on the surface of a T cell. An antigen-presenting matrix can be on the surface of an antigen-presenting cell (APC), on a vesicle preparation of an APC, or can be in the form of a synthetic matrix on a solid support such as a bead or a plate. An example of a synthetic antigen-presenting matrix is purified MHC class I molecules complexed to β2-microglobulin, multimers of such purified MHC class I molecules, purified MHC Class II molecules, or functional portions thereof, attached to a solid support.

The term "antigen presenting cells (APC)" refers to a class of cells capable of presenting one or more antigens in the form of antigen-MHC complex recognizable by specific effector cells of the immune system, and thereby inducing an effective cellular immune response against the antigen or antigens being presented. While many types of cells may be capable of presenting antigens on their cell surface for T-cell recognization, only professional APCs have the capacity to present antigens in an efficient amount and further to activate T-cells for cytotoxic T-lymphocyte (CTL) responses. APCs can be intact whole cells such as marcrophages, B-cells and dendritic cells; or other molecules, naturally occurring or synthetic, such as purified MHC class I molecules complexed to β2-microglobulin.

The term "dendritic cells (DC)" refers to a diverse population of morphologically similar cell types found in a variety of lymphoid and non-lymphoid tissues (Steinman (1991) Ann. Rev. Immunol. 9:271–296). Dendritic cells constitute the most potent and preferred APCs in the organism. A subset, if not all, of dendritic cells are derived from bone marrow progenitor cells, circulate in small numbers in the peripheral blood and appear either as immature Langerhans' cells or terminally differentiated mature cells. While the dendritic cells can be differentiated from monocytes, they possess distinct phenotypes. For example, a particular differentiating marker, CD14 antigen, is not found in dendritic cells but is possessed by monocytes. Also, mature dendritic cells are not phagocytic, whereas the monocytes are strongly phagocytosing cells. It has been shown that DCs provide all the signals necessary for T cell activation and proliferation.

The terms "antigen presenting cell recruitment factors" or "APC recruitment factors" includes both intact, whole cells as well as other molecules which are capable of recruiting antigen presenting cells. Examples of suitable APC recruitment factors include molecules such as interleukin 4 (IL4), granulocyte monocyte colony stimulating factor (GM-CSF), Sepragel and macrophage inflammatory protein 3 alpha (MIP3). These are available from Immunex, Schering-Plough and R&D Systems (Minneapolis, Minn.). They also can be recombinantly produced using the methods disclosed in Current Protocols in Molecular Biology (F. M. Ausubel et al., eds., (1987)). Peptides, proteins and compounds having the same biological activity as the above-noted factors are included within the scope of this invention.

The term "immune effector cells" refers to cells capable of binding an antigen and which mediate an immune response. These cells include, but are not limited to, T cells, B cells, monocytes, macrophages, NK cells and cytotoxic T lymphocytes (CTLs), for example CTL lines, CTL clones, and CTLs from tumor, inflammatory, or other infiltrates. Certain diseased tissue expresses specific antigens and CTLs specific for these antigens have been identified. For example, approximately 80% of melanomas express the antigen known as GP- 100.

The term "immune effector molecule" as used herein, refers to molecules capable of antigen-specific binding, and includes antibodies, T cell antigen receptors, and MHC Class I and Class II molecules.

A "naïve" immune effector cell is an immune effector cell that has never been exposed to an antigen.

As used herein, the term "educated, antigen-specific immune effector cell", is an immune effector cell as defined above, which has encountered antigen and which is specific for that antigen. An educated, antigen-specific immune effector cell may be activated upon binding antigen. "Activated" implies that the cell is no longer in $G_0$ phase, and begins to produce cytokines characteristic of the cell type. For example, activated CD4+T cells secrete IL-2 and have a higher number of high affinity IL-2 receptors on their cell surfaces relative to resting CD4+T cells.

A peptide or polypeptide of the invention may be preferentially recognized by antigen-specific immune effector cells, such as B cells and T cells. In the context of T cells, the term "recognized" intends that a peptide or polypeptide of the invention, comprising one or more synthetic antigenic epitopes, is recognized, i.e., is presented on the surface of an APC together with (i.e., bound to) an MHC molecule in such a way that a T cell antigen receptor (TCR) on the surface of an antigen-specific T cell binds to the epitope wherein such binding results in activation of the T cell. The term "preferentially recognized" intends that a polypeptide of the invention is substantially not recognized, as defined above, by a T cell specific for an unrelated antigen. Assays for determining whether an epitope is recognized by an antigen-specific T cell are known in the art and are described herein.

As used herein, the term "inducing an immune response in a subject" is a term well understood in the art and intends that an increase of at least about 2-fold, more preferably at least about 5-fold, more preferably at least about 10-fold, more preferably at least about 100-fold, even more preferably at least about 500-fold, even more preferably at least about 1000-fold or more in an immune response to an antigen (or epitope) can be detected or measured, after introducing the antigen (or epitope) into the subject, relative to the immune response (if any) before introduction of the antigen (or epitope) into the subject. An immune response to an antigen (or epitope), includes, but is not limited to, production of an antigen-specific (or epitope-specific) antibody, and production of an immune cell expressing on its surface a molecule which specifically binds to an antigen (or epitope). Methods of determining whether an immune response to a given antigen (or epitope) has been induced are well known in the art. For example, antigen-specific antibody can be detected using any of a variety of immunoassays known in the art, including, but not limited to, ELISA, wherein, for example, binding of an antibody in a sample to an immobilized antigen (or epitope) is detected with a detectably-labeled second antibody (e.g., enzyme-labeled mouse anti-human Ig antibody). "Co-stimulatory molecules" are involved in the interaction between receptor-ligand pairs expressed on the surface of antigen presenting cells and T cells. Research accumulated over the past several years has demonstrated convincingly that resting T cells require at least two signals for induction of cytokine gene expression and proliferation (Schwartz R. H. (1990) Science 248:1349–1356 and Jenkins M. K. (1992) Immunol. Today 13:69–73). One signal, the one that confers specificity, can be produced by interaction of the TCR/CD3 complex with an appropriate MHC/peptide complex. The second signal is not antigen specific and is termed the "co-stimulatory" signal. This signal was originally defined as an activity provided by bone-marrow-derived accessory cells such as macrophages and dendritic cells, the so called "professional" APCs. Several molecules have been shown to enhance co-stimulatory activity. These are heat stable antigen (HSA) (Liu Y. et al. (1992) J. Exp. Med. 175:437–445), chondroitin sulfate-modified MHC invariant chain (Ii-CS) (Naujokas M. F. et al. (1993) Cell 74:257–268), intracellular adhesion molecule 1 (ICAM-1) (Van Seventer G. A. (1990) J. Immunol. 144:4579–4586), B7-1, and B7-2/B70 (Schwartz R. H. (1992) Cell 71:1065–1068). These molecules each appear to assist co-stimulation by interacting with their cognate ligands on the T cells. Co-stimulatory molecules mediate co-stimulatory signal(s) which are necessary, under normal physiological conditions, to achieve full activation of naive T cells. One exemplary receptor-ligand pair is the B7 co-stimulatory molecule on the surface of APCs and its counter-receptor CD28 or CTLA-4 on T cells (Freeman et al. (1993) Science 262:909–911; Young et al. (1992) J. Clin. Invest. 90:229 and Nabavi et al. (1992) Nature 360:266–268). Other important co-stimulatory molecules are CD40, CD54, CD80, CD86. The term "co-stimulatory molecule" encompasses any single molecule or combination of molecules which, when acting together with a peptide/MHC complex bound by a TCR on the surface of a T cell, provides a co-stimulatory effect which achieves activation of the T cell that binds the peptide. The term thus encompasses B7, or other co-stimulatory molecule(s) on an antigen-presenting matrix such as an APC, fragments thereof (alone, complexed with another molecule(s), or as part of a fusion protein) which, together with peptide/MHC complex, binds to a cognate ligand and results in activation of the T cell when the TCR on the surface of the T cell specifically binds the peptide. Co-stimulatory molecules are commercially available from a variety of sources, including, for example, Beckman Coulter, Inc. (Fullerton, Calif.). It is intended, although not always explicitly stated, that molecules having similar biological activity as wild-type or purified co-stimulatory molecules (e.g., recombinantly produced or muteins thereof) are intended to be used within the spirit and scope of the invention.

As used herein, "solid phase support" or "solid support", used interchangeably, is not limited to a specific type of support. Rather a large number of supports are available and are known to one of ordinary skill in the art. Solid phase supports include silica gels, resins, derivatized plastic films, glass beads, cotton, plastic beads, alumina gels. As used herein, “solid support” also includes synthetic antigen-presenting matrices, cells, and liposomes. A suitable solid phase support may be selected on the basis of desired end use and suitability for various protocols. For example, for peptide synthesis, solid phase support may refer to resins such as polystyrene (e.g., PAM-resin obtained from Bachem Inc., Peninsula Laboratories, etc.), POLYHIPE® resin (obtained from Aminotech, Canada), polyamide resin (obtained from Peninsula Laboratories), polystyrene resin grafted with polyethylene glycol (TentaGel®, Rapp Polymere, Tubingen, Germany) or polydimethylacrylamide resin (obtained from Milligen/Biosearch, California).

The term “immunomodulatory agent”, as used herein, is a molecule, a macromolecular complex, or a cell that modulates an immune response and encompasses a synthetic antigenic peptide of the invention alone or in any of a variety of formulations described herein; a polypeptide comprising a synthetic antigenic peptide of the invention; a polynucleotide encoding a peptide or polypeptide of the invention; a synthetic antigenic peptide of the invention bound to a Class I or a Class II MHC molecule on an antigen-presenting matrix, including an APC and a synthetic antigen-presenting matrix (in the presence or absence of co-stimulatory molecule(s)); a synthetic antigenic peptide of the invention covalently or non-covalently complexed to another molecule(s) or macromolecular structure; and an educated, antigen-specific immune effector cell which is specific for a peptide of the invention.

The term “modulate an immune response” includes inducing (increasing, eliciting) an immune response; and reducing (suppressing) an immune response. An immunomodulatory method (or protocol) is one that modulates an immune response in a subject.

As used herein, the term “cytokine” refers to any one of the numerous factors that exert a variety of effects on cells, for example, inducing growth or proliferation. Non-limiting examples of cytokines which may be used alone or in combination in the practice of the present invention include, interleukin-2 (IL-2), stem cell factor (SCF), interleukin 3 (IL-3), interleukin 6 (IL-6), interleukin 12 (IL-12), G-CSF, granulocyte macrophage-colony stimulating factor (GM-CSF), interleukin-1 alpha (IL-1I), interleukin-11 (IL-11), MIP-1I, leukemia inhibitory factor (LIF), c-kit ligand, thrombopoietin (TPO) and flt3 ligand. The present invention also includes culture conditions in which one or more cytokine is specifically excluded from the medium. Cytokines are commercially available from several vendors such as, for example, Genzyme (Framingham, Mass.), Genentech (South San Francisco, Calif.), Amgen (Thousand Oaks, Calif.), R&D Systems (Minneapolis, Minn.) and Immunex (Seattle, Wash.). It is intended, although not always explicitly stated, that molecules having similar biological activity as wild-type or purified cytokines (e.g., recombinantly produced or muteins thereof) are intended to be used within the spirit and scope of the invention.

The terms “polynucleotide” and “nucleic acid molecule” are used interchangeably to refer to polymeric forms of nucleotides of any length. The polynucleotides may contain deoxyribonucleotides, ribonucleotides, and/or their analogs. Nucleotides may have any three-dimensional structure, and may perform any function, known or unknown. The term “polynucleotide” includes, for example, single-, double-stranded and triple helical molecules, a gene or gene fragment, exons, introns, MRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A nucleic acid molecule may also comprise modified nucleic acid molecules.

The term “peptide” is used in its broadest sense to refer to a compound of two or more subunit amino acids, amino acid analogs, or peptidomimetics. The subunits may be linked by peptide bonds. In another embodiment, the subunit may be linked by other bonds, e.g. ester, ether, etc. As used herein the term “amino acid” refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is commonly called a polypeptide or a protein.

The term “genetically modified” means containing and/or expressing a foreign gene or nucleic acid sequence which in turn, modifies the genotype or phenotype of the cell or its progeny. In other words, it refers to any addition, deletion or disruption to a cell’s endogenous nucleotides.

As used herein, “expression” refers to the process by which polynucleotides are transcribed into mRNA and translated into peptides, polypeptides, or proteins. If the polynucleotide is derived from genomic DNA, expression may include splicing of the mRNA, if an appropriate eukaryotic host is selected. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgamo sequence and the start codon AUG (Sambrook et al. (1989) supra ). Similarly, an eukaryotic expression vector includes a heterologous or homologous promoter for RNA polymerase II, a downstream polyadenylation signal, the start codon AUG, and a termination codon for detachment of the ribosome. Such vectors can be obtained commercially or assembled by the sequences described in methods well known in the art, for example, the methods described below for constructing vectors in general.

“Under transcriptional control” is a term well understood in the art and indicates that transcription of a polynucleotide sequence, usually a DNA sequence, depends on its being operably (operatively) linked to an element which contributes to the initiation of, or promotes, transcription. “Operably linked” refers to a juxtaposition wherein the elements are in an arrangement allowing them to function.

A “gene delivery vehicle” is defined as any molecule that can carry inserted polynucleotides into a host cell. Examples of gene delivery vehicles are liposomes, biocompatible polymers, including natural polymers and synthetic polymers; lipoproteins; polypeptides; polysaccharides; lipopolysaccharides; artificial viral envelopes; metal particles; and bacteria, viruses, such as baculovirus, adenovirus and retrovirus, bacteriophage, cosmid, plasmid, fingal vectors and other recombination vehicles typically used in the art which have been described for expression in a variety of eukaryotic and prokaryotic hosts, and may be used for gene therapy as well as for simple protein expression.

“Gene delivery,” “gene transfer,” and the like as used herein, are terms referring to the introduction of an exogenous polynucleotide (sometimes referred to as a “transgene”) into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art and described herein.

A "viral vector" is defined as a recombinantly produced virus or viral particle that comprises a polynucleotide to be delivered into a host cell, either in vivo, ex vivo or in vitro. Examples of viral vectors include retroviral vectors, adenovirus vectors, adeno-associated virus vectors and the like. In aspects where gene transfer is mediated by a retroviral vector, a vector construct refers to the polynucleotide comprising the retroviral genome or part thereof, and a therapeutic gene. As used herein, "retroviral mediated gene transfer" or "retroviral transduction" carries the same meaning and refers to the process by which a gene or nucleic acid sequences are stably transferred into the host cell by virtue of the virus entering the cell and integrating its genome into the host cell genome. The virus can enter the host cell via its normal mechanism of infection or be modified such that it binds to a different host cell surface receptor or ligand to enter the cell. As used herein, retroviral vector refers to a viral particle capable of introducing exogenous nucleic acid into a cell through a viral or viral-like entry mechanism.

Retroviruses carry their genetic information in the form of RNA; however, once the virus infects a cell, the RNA is reverse-transcribed into the DNA form which integrates into the genomic DNA of the infected cell. The integrated DNA form is called a provirus.

In aspects where gene transfer is mediated by a DNA viral vector, such as an adenovirus (Ad) or adeno-associated virus (AAV), a vector construct refers to the polynucleotide comprising the viral genome or part thereof, and a transgene. Adenoviruses (Ads) are a relatively well characterized, homogenous group of viruses, including over 50 serotypes. (see, e.g., WO 95/27071). Ads are easy to grow and do not require integration into the host cell genome. Recombinant Ad-derived vectors, particularly those that reduce the potential for recombination and generation of wild-type virus, have also been constructed. (see WO 95/00655 and WO 95/11984). Wild-type AAV has high infectivity and specificity integrating into the host cell's genome. Hermonat and Muzyczka (1984) Proc. Natl. Acad. Sci. 81:6466–6470 and Lebkowski et al. (1988) Mol. Cell. Biol. 8:3988–3996.

Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

Gene delivery vehicles also include several non-viral vectors, including DNA/liposome complexes, and targeted viral protein-DNA complexes. Liposomes that also comprise a targeting antibody or fragment thereof can be used in the methods of this invention. To enhance delivery to a cell, the nucleic acid or proteins of this invention can be conjugated to antibodies or binding fragments thereof which bind cell surface antigens, e.g., TCR, CD3 or CD4.

Hybridization refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions of about 6×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15M NaCl and 15 mM citrate buffer. It is understood that equivalents of SSC using other buffer systems can be employed.

A polynucleotide or polynucleotide region (or a polypeptide or polypeptide region) has a certain percentage (for example, 80%, 85%, 90%, or 95%) of "sequence identity" to another sequence means that, when aligned, that percentage of bases (or amino acids) are the same in comparing the two sequences. This alignment and the percent homology or sequence identity can be determined using software programs known in the art, for example those described in CURRENT PROTOCOLS IN MOLECULAR BIOLOGY (F. M. Ausubel et al., eds., 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by HIGH SCORE; Databases=non-redundant, GenBank+EMBL+DDBJ+PDB+GenBank CDS translations+SwissProtein+SPupdate+PIR. Details of these programs can be found at the following Internet address: www.ncbi.nlm.nih.gov/cgi-bin/BLAST.

"In vivo" gene delivery, gene transfer, gene therapy and the like as used herein, are terms referring to the introduction of a vector comprising an exogenous polynucleotide directly into the body of an organism, such as a human or non-human mammal, whereby the exogenous polynucleotide is introduced to a cell of such organism in vivo.

The term "isolated" means separated from constituents, cellular and otherwise, in which the polynucleotide, peptide, polypeptide, protein, antibody, or fragments thereof, are normally associated with in nature. For example, with respect to a polynucleotide, an isolated polynucleotide is one that is separated from the 5' and 3' sequences with which it is normally associated in the chromosome. As is apparent to those of skill in the art, a non-naturally occurring polynucleotide, peptide, polypeptide, protein, antibody, or fragments thereof, does not require "isolation" to distinguish it from its naturally occurring counterpart. In addition, a "concentrated", "separated" or "diluted" polynucleotide, peptide, polypeptide, protein, antibody, or fragments thereof, is distinguishable from its naturally occurring counterpart in that the concentration or number of molecules per volume is greater than "concentrated" or less than "separated" than that of its naturally occurring counterpart. A polynucleotide, peptide, polypeptide, protein, antibody, or fragments thereof, which differs from the naturally occurring counterpart in its primary sequence or for example, by its glycosylation pattern, need not be present in its isolated form since it is distinguishable from its naturally occurring counterpart by its primary sequence, or alternatively, by another characteristic such as glycosylation pattern. Although not explicitly stated for each of the inventions disclosed herein, it is to be understood that all of the above embodiments for each of the compositions disclosed below and under the appropriate conditions, are provided by this invention. Thus, a non-naturally occurring polynucleotide is provided as a separate embodiment from the isolated naturally occurring polynucleotide. A protein produced in a bacterial cell is provided as a separate embodiment from the naturally occurring protein isolated from a eucaryotic cell in which it is produced in nature.

"Host cell","target cell" or "recipient cell" are intended to include any individual cell or cell culture which can be or have been recipients for vectors or the incorporation of exogenous nucleic acid molecules, polynucleotides and/or proteins. It also is intended to include progeny of a single cell, and the progeny may not necessarily be completely identical (in morphology or in genomic or total DNA complement) to the original parent cell due to natural, accidental, or deliberate mutation. The cells may be procaryotic or eucaryotic, and include but are not limited to bacterial cells, yeast cells, animal cells, and mammalian cells, e.g., murine, rat, simian or human.

A "subject" is a vertebrate, preferably a mammal, more preferably a human. Mammals include, but are not limited to, murines, simians, humans, farm animals, sport animals, and pets.

A "control" is an alternative subject or sample used in an experiment for comparison purpose. A control can be "positive" or "negative". For example, where the purpose of the experiment is to determine a correlation of an altered expression level of a gene with a particular type of cancer, it is generally preferable to use a positive control (a subject or a sample from a subject, carrying such alteration and exhibiting syndromes characteristic of that disease), and a negative control (a subject or a sample from a subject lacking the altered expression and clinical syndrome of that disease).

The terms "cancer," "neoplasm," and "tumor," used interchangeably and in either the singular or plural form, refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by such procedures as CAT scan, magnetic resonance imaging (MRI), X-ray, ultrasound or palpation. Biochemical or immunologic findings alone may be insufficient to meet this definition.

"Suppressing" tumor growth indicates a growth state that is curtailed compared to growth without contact with educated, antigen-specific immune effector cells described herein. Tumor cell growth can be assessed by any means known in the art, including, but not limited to, measuring tumor size, determining whether tumor cells are proliferating using a $^{3}$H-thymidine incorporation assay, or counting tumor cells. "Suppressing" tumor cell growth means any or all of the following states: slowing, delaying, and "suppressing" tumor growth indicates a growth state that is curtailed when stopping tumor growth, as well as tumor shrinkage.

The term "culturing" refers to the in vitro propagation of cells or organisms on or in media of various kinds. It is understood that the descendants of a cell grown in culture may not be completely identical (morphologically, genetically, or phenotypically) to the parent cell. By "expanded" is meant any proliferation or division of cells.

A "composition" is intended to mean a combination of active agent and another compound or composition, inert (for example, a detectable agent or label) or active, such as an adjuvant.

A "pharmaceutical composition" is intended to include the combination of an active agent with a carrier, inert or active, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin REMINGTON'S PHARM. SCI., 15th Ed. (Mack Publ. Co., Easton (1975)).

An "effective amount" is an amount sufficient to effect beneficial or desired results. An effective amount can be administered in one or more administrations, applications or dosages.

The present invention provides compounds having the following structure:

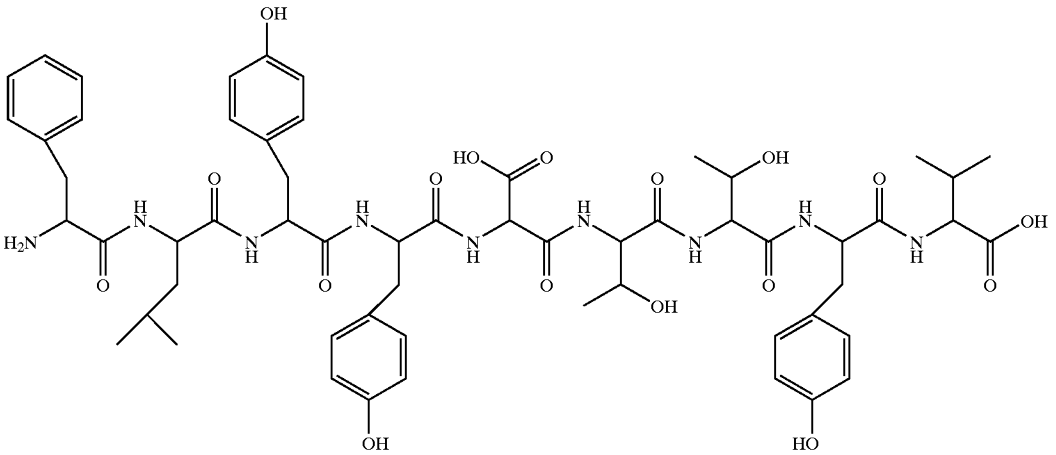

or

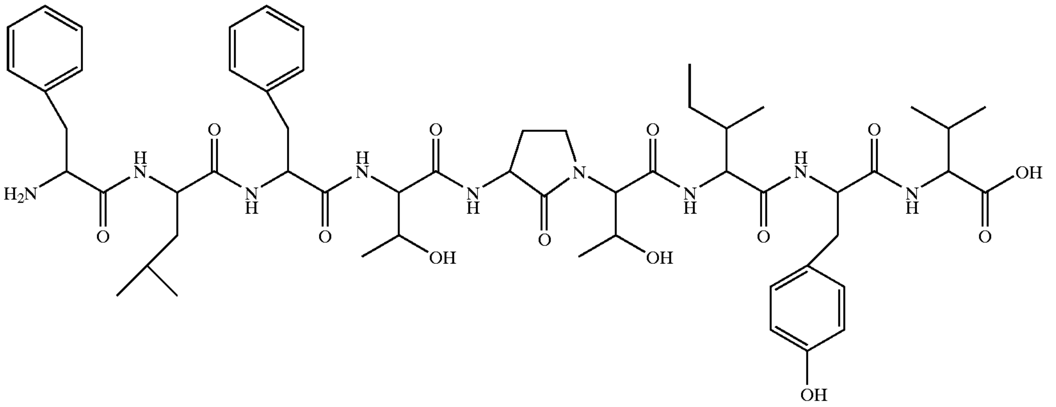

or

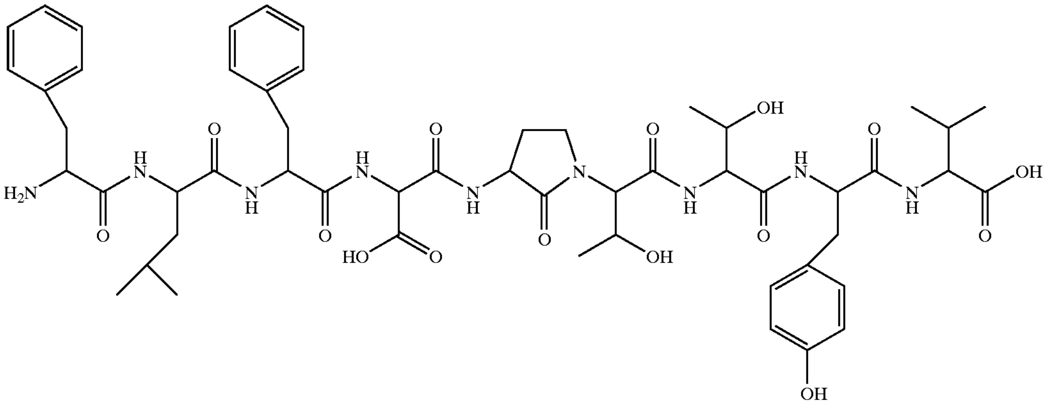

The present invention also provides novel synthetic antigenic peptides designed for enhanced binding to MHC molecules and useful for modulating immune responses to the synthetic peptide epitope and the corresponding native peptides from which they are derived. The synthetic antigenic peptide epitope sequences of the present invention differ from their natural counterparts in at that they contain alterations in amino acid sequence, relative to the native sequence, in the MHC Class I binding domain, thereby conferring tighter binding to the MHC. They further contain mutations in the putative T cell receptor-binding domain, resulting in an increased affinity for the T cell antigen receptor. These differences from the native sequence confer advantages in the methods of the present invention over the native sequence, in that the synthetic antigenic peptide epitopes of the invention have enhanced immunomodulatory properties.

This invention provides novel, synthetic antigenic peptide sequences, which are useful as components of anti-cancer vaccines and to expand immune effector cells that are specific for cancers characterized by expression of the HER2 gene. The peptides, FLYYGTTYV (SEQ ID NO:3), FLFTPTIYV (SEQ ID NO:5), and FLFDPTTYV (SEQ ID NO:7) differ from the natural epitope, MAGVGSPYV (SEQ ID NO:9), in two ways: (1) they contain mutations at position 1 in the putative HLA-A2 binding domain (amino acid residues 1, 2, and 9) conferring tighter binding to the MHC, and (2) they contain mutations in the putative T cell receptor-binding domain (amino acid residues 3–8) likely resulting in an increased avidity for the T cell receptor.

Binding of synthetic antigenic peptide of the invention to an MHC Class I molecule can be measured by methods that are known in the art and include, but are not limited to, calculating the affinity based on an algorithm (see, for example, Parker et al. (1992) J. Immunol. 149:3580–3587); and experimentally determining binding affinity (see, for example, Tan et al. (1997) J. Immunol. Meth. 209(1):25–36. For example, the relative binding of a peptide to a Class I molecule can be measured on the basis of binding of a radiolabeled standard peptide to detergent-solubilized MHC molecules, using various concentrations of test peptides (e.g., ranging from 100 mM to 1 nM). MHC Class I heavy chain and β2-microglobulin are coincubated with a fixed concentration (e.g., 5 nM) radiolabeled standard (control) peptide and various concentrations of a test peptide for a suitable period of time (e.g., 2 hours to 72 hours) at room temperature in the presence of a mixture of protease inhibitors. A control tube contains standard peptide and MHC molecules, but no test peptide. The percent MHC-bound radioactivity is determined by gel filtration. The IC50 (concentration of test peptide which results in 50% inhibition of binding of control peptide) is calculated for each peptide.

Synthetic peptides of the invention also may bind to a TCR with a higher affinity than the "natural" sequence. Methods for determining binding affinity to a TCR are known in the art and include, but are not limited to, those described in al-Ramadi et al. (1992) J. Imunol. 155(2):662–673; and Zuegel et al. (1998) J. Immunol. 161(4):1705–1709.

Further encompassed by the term "synthetic antigenic peptide" are multimers (concatemers) of a synthetic antigenic peptide of the invention, optionally including intervening amino acid sequences as well as polypeptides comprising the sequences FLYYGTTYV (SEQ ID NO:3) FLFTPTIYV (SEQ ID NO:5), and FLFDPTTYV (SEQ ID NO:7). The invention also provides polypeptides comprising these sequences wherein the polypeptides are preferentially recognized by HER2 specific cytotoxic T lymphocytes.

Polypeptides comprising the peptide sequences of the invention can be prepared by altering the sequence of polynucleotides that encode the native HER2 polypeptide sequence. This is accomplished by methods of recombinant DNA technology well know to those skilled in the art. For example, site directed mutagenesis can be performed on recombinant polynucleotides encoding the native HER2 sequence to introduce changes in the polynucleotide sequence so that the altered polynucleotide encodes the peptides of the invention.

The proteins and polypeptides of this invention can be obtained by chemical synthesis using a commercially available automated peptide synthesizer such as those manufactured by Perkin Elmer/Applied Biosystems, Inc., Model 430A or 431A, Foster City, Calif., USA. The synthesized protein or polypeptide can be precipitated and further purified, for example by high performance liquid chromatography (HPLC). Accordingly, this invention also provides a process for chemically synthesizing the proteins of this invention by providing the sequence of the protein and reagents, such as amino acids and enzymes and linking together the amino acids in the proper orientation and linear sequence.

Alternatively, the proteins and polypeptides can be obtained by well-known recombinant methods as described herein using the host cell and vector systems described below.

Peptide Analogues

It is well know to those skilled in the art that modifications can be made to the peptides of the invention to provide them with altered properties. As used herein the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is commonly called a polypeptide or a protein.

Peptides of the invention can be modified to include unnatural amino acids. Thus, the peptides may comprise D-amino acids, a combination of D- and L-amino acids, and various "designer" amino acids (e.g., β-methyl amino acids, Cα-methyl amino acids, and Nα-methyl amino acids, etc.) to convey special properties to peptides. Additionally, by assigning specific amino acids at specific coupling steps, peptides with α-helices β turns, β sheets, γ-turns, and cyclic peptides can be generated. Generally, it is believed that α-helical secondary structure or random secondary structure is preferred.

In a further embodiment, subunits of peptides that confer useful chemical and structural properties will be chosen. For example, peptides comprising D-amino acids will be resistant to L-amino acid-specific proteases in vivo. Modified compounds with D-amino acids may be synthesized with the amino acids aligned in reverse order to produce the peptides of the invention as retro-inverso peptides. In addition, the present invention envisions preparing peptides that have more well-defined structural properties, and the use of peptidomimetics, and peptidomimetic bonds, such as ester bonds, to prepare peptides with novel properties. In another embodiment, a peptide may be generated that incorporates a reduced peptide bond, i.e., $R_1$—$CH_2NH$—$R_2$, where $R_1$, and $R_2$ are amino acid residues or sequences. A reduced peptide bond may be introduced as a dipeptide subunit. Such a molecule would be resistant to peptide bond hydrolysis, e.g., protease activity. Such molecules would provide ligands with unique function and activity, such as extended half-lives in vivo due to resistance to metabolic breakdown, or protease activity. Furthermore, it is well known that in certain systems constrained peptides show enhanced functional activity (Hruby (1982) Life Sciences 31:189–199; Hruby et al. (1990) Biochem J. 268:249–262); the present invention provides a method to produce a constrained peptide that incorporates random sequences at all other positions.

Non-classical Amino Acids that Induce Conformational Constraints

The following non classical amino acids may be incorporated in the peptides of the invention in order to introduce particular conformational motifs: 1,2,3,4-tetrahydroisoquinoline-3-carboxylate (Kazmierski et al. (1991) J. Am. Chem. Soc. 113:227S–2283); (2S,3S)-methyl-phenylalanine, (2S,3R)- methyl-phenylalanine, (2R,3S)-methyl-phenylalanine and (2R,3R)-methyl-phenylalanine (Kazmierski and Hruby (1991) Tetrahedron Lett. ?); 2-aminotetrahydronaphthalene-2-carboxylic acid (Landis (1989) Ph.D. Thesis, University of Arizona); hydroxy-1,2,3,4-tetrahydroisoquinoline-3-carboxylate (Miyake et al. (1989) J. Takeda Res. Labs 43:53–76). (histidine isoquinoline carboxylic acid) (Zechel et al. (1991) Int. J. Pep. Protein Res. 43?; and HIC (histidine cyclic urea) (Dharanipragada).

The following amino acid analogs and peptidomimetics may be incorporated into a peptide to induce or favor specific secondary structures: LL-Acp (LL-3-amino-2-propenidone-6-carboxylic acid), a β-turn inducing dipeptide analog (Kemp et al. (1985) J. Org. Chem. 50:5834–5838); β-sheet inducing analogs (Kemp et al. (1988) Tetrahedron Lett. 29:5081–5082); β-turn inducing analogs (Kemp et al. (1988) Tetrahedron Lett. 29:5057–5060); α-helix inducing analogs (Kemp et al. (1988) Tetrahedron Lett. 29:4935–4938); γ-turn inducing analogs (Kemp et al. (1989) J. Org. Chem. 54:109:115); and analogs provided by the following references: Nagai and Sato (1985) Tetrahedron Lett. 26:647–650; DiMaio et al. (1989) J. Chem. Soc. Perkin Trans. p. 1687; also a Gly-Ala turn analog (Kahn et al. (1989) Tetrahedron Lett. 30:2317); amide bond isostere (clones et al. (1988) Tetrahedron Lett. 29:38S3–38S6); tretrazol (Zabrocki et al. (1988) J. Am. Chem. Soc. 110:587S–5880); DTC (Samanen et al. (1990) Int. J. Protein Pep. Res. 35:501:509); and analogs taught in Olson et al. (1990) J. Am. Chem. Sci. 112:323–333 and Garvey et al. (1990) J. Org. Chem. 56:436. Conformationally restricted mimetics of beta turns and beta bulges, and peptides containing them, are described in U.S. Pat. No. 5,440,013, issued Aug. 8, 1995 to Kahn.

Determination of the sequence of peptides that incorporate such non-classical amino acids is readily accomplished by the use of a coded library. Alternatively, a combination of initial Edman degradation followed by amino acid analysis of the residual chain can be used to determine the structure of a peptide with desired activity. Mass spectral analysis may be employed.

A synthetic antigenic peptide epitope of the invention can be used in a variety of formulations, which may vary depending on the intended use.

A synthetic antigenic peptide epitope of the invention can be covalently or non-covalently linked (complexed) to various other molecules, the nature of which may vary depending on the particular purpose. For example, a peptide of the invention can be covalently or non-covalently complexed to a macromolecular carrier, including, but not limited to, natural and synthetic polymers, proteins, polysaccharides, poly(amino acid), polyvinyl alcohol, polyvinyl pyrrolidone, and lipids. A peptide can be conjugated to a fatty acid, for introduction into a liposome. U.S. Pat. No. 5,837,249. A synthetic peptide of the invention can be complexed covalently or non-covalently with a solid support, a variety of which are known in the art. A synthetic antigenic peptide epitope of the invention can be associated with an antigen-presenting matrix with or without co-stimulatory molecules, as described in more detail below.

Examples of protein carriers include, but are not limited to, superantigens, serum albumin, tetanus toxoid, ovalbumin, thyroglobulin, myoglobulin, and immunoglobulin.

Peptide-protein carrier polymers may be formed using conventional crosslinking agents such as carbodiimides. Examples of carbodiimides are 1-cyclohexyl-3-(2-morpholinyl-(4-ethyl) carbodiimide (CMC), 1-ethyl-3-(3-dimethyaminopropyl) carbodiimide (EDC) and 1-ethyl-3-(4-azonia-44-dimethylpentyl) carbodiimide.

Examples of other suitable crosslinking agents are cyanogen bromide, glutaraldehyde and succinic anhydride. In general, any of a number of homobifunctional agents including a homobifunctional aldehyde, a homobifunctional epoxide, a homobifinctional imidoester, a homobifinctional N-hydroxysuccinimide ester, a homobifinctional maleimide, a homobifunctional alkyl halide, a homobifunctional pyridyl disulfide, a homobifinctional aryl halide, a homobifimctional hydrazide, a homobi functional diazonium derivative and a homobifinctional photoreactive compound may be used. Also included are heterobifunctional compounds, for example, compounds having an amine-reactive and a sulfhydryl-reactive group, compounds with an amine-reactive and a photoreactive group and compounds with a carbonyl-reactive and a sulfhydryl-reactive group.

Specific examples of such homobifunctional crosslinking agents include the bifunctional N-hydroxysuccinimide esters dithiobis(succinimidylpropionate), disuccinimidyl suberate, and disuccinimidyl tartarate; the bifunctional imidoesters dimethyl adipimidate, dimethyl pimelimidate, and dimethyl suberimidate; the bifunctional sulfhydryl-reactive crosslinkers 1,4-di-[3'-(2'-pyridyldithio) propion-amido] butane, bismaleimidohexane, and bis-N-maleimido-1,8-octane; the bifunctional aryl halides 1,5-difluoro-2,4-dinitrobenzene and 4,4'-difluoro-3,3'-dinitrophenylsulfone; bifunctional photoreactive agents such as bis-[b-(4-azidosalicylamido)ethyl]disulfide; the bifunctional aldehydes formaldehyde, malondialdehyde, succinaldehyde, glutaraldehyde, and adipaldehyde; a bifunctional epoxide such as 1,4-butaneodiol diglycidyl ether, the bifunctional hydrazides adipic acid dihydrazide, carbohydrazide, and succinic acid dihydrazide; the bifunctional diazoniums o-tolidine, diazotized and bis-diazotized benzidine; the bifunctional alkylhalides N1N'-ethylene-bis (iodoacetamide), N1N'-hexamethylene-bis(iodoacetamide), N1N'-undecamethylene-bis(iodoacetamide), as well as benzylhalides and halomustards, such as ala'-diiodo-p-xylene sulfonic acid and tri(2-chloroethyl)amine, respectively.

Examples of other common heterobifunctional crosslinking agents that may be used to effect the conjugation of proteins to peptides include, but are not limited to, SMCC succinimidyl-4-(N-maleimidomethyl)cyclohexane-1-carboxylate), MBS (m-maleimidobenzoyl-N-hydroxysuccinimide ester), SIAB (N-succinimidyl(4-iodoacteyl)aminobenzoate), SMPB (succinimidyl-4-(p-maleimidophenyl)butyrate), GMBS (N-(γ-maleimidobutyryloxy)succinimide ester), MPBH (4-(4-N-maleimidopohenyl) butyric acid hydrazide), M2C2H (4-(N-maleimidomethyl) cyclohexane-1-carboxyl-hydrazide), SMPT (succinimidyloxycarbonyl-à-methyl-à-(2-pyridyldithio)toluene), and SPDP (N-succinimidyl 3-(2-pyridyldithio)propionate).

Crosslinking may be accomplished by coupling a carbonyl group to an amine group or to a hydrazide group by reductive amination.

Peptides of the invention also may be formulated as non-covalent attachment of monomers through ionic, adsorptive, or biospecific interactions. Complexes of peptides with highly positively or negatively charged molecules may be done through salt bridge formation under low ionic strength environments, such as in deionized water. Large complexes can be created using charged polymers such as poly-(L-glutamic acid) or poly-(L-lysine) which contain numerous negative and positive charges, respectively. Adsorption of peptides may be done to surfaces such as microparticle latex beads or to other hydrophobic polymers, forming non-covalently associated peptide-superantigen complexes effectively mimicking crosslinked or chemically polymerized protein. Finally, peptides may be non-covalently linked through the use of biospecific interactions between other molecules. For instance, utilization of the strong affmity of biotin for proteins such as avidin or streptavidin or their derivatives could be used to form peptide complexes. These biotin-binding proteins contain four binding sites that can interact with biotin in solution or be covalently attached to another molecule. Wilchek (1988) Anal Biochem. 171:1–32. Peptides can be modified to possess biotin groups using common biotinylation reagents such as the N-hydroxysuccinimidyl ester of D-biotin (NHS-biotin) which reacts with available amine groups on the protein. Biotinylated peptides then can be incubated with avidin or streptavidin to create large complexes. The molecular mass of such polymers can be regulated through careful control of the molar ratio of biotinylated peptide to avidin or streptavidin.

Also provided by this application are the peptides and polypeptides described herein conjugated to a detectable agent for use in the diagnostic methods. For example, detectably labeled peptides and polypeptides can be bound to a column and used for the detection and purification of antibodies. They also are useful as immunogens for the production of antibodies, as described below.

The peptides of this invention also can be combined with various liquid phase carriers, such as sterile or aqueous solutions, pharmaceutically acceptable carriers, suspensions and emulsions. Examples of non-aqueous solvents include propyl ethylene glycol, polyethylene glycol and vegetable oils. When used to prepare antibodies, the carriers also can include an adjuvant that is useful to non-specifically augment a specific immune response. A skilled artisan can easily determine whether an adjuvant is required and select one. However, for the purpose of illustration only, suitable adjuvants include, but are not limited to, Freund's Complete and Incomplete, mineral salts and polynucleotides.

This invention further provides polynucleotides (SEQ ID NOS:4,6,8) encoding polypeptides comprising the sequences FLYYGTTYV (SEQ ID NO:3) FLFTPTIYV (SEQ ID NO:5), and FLFDPTTYV (SEQ ID NO:7) and the complements of these polynucleotides. As used herein, the term "polynucleotide" encompasses DNA, RNA and nucleic acid mimetics. In addition to the sequences shown in SEQ ID NOS 4, 6 and 8, or their complements, this invention also provides the anti-sense polynucleotide stand, e.g. antisense RNA to these sequences or their complements. One can obtain an antisense RNA using the sequences provided in SEQ ID NOS 4, 6 and 8, and the methodology described in Vander Krol, et al. (1988) BioTechniques 6:958.

The polynucleotides of this invention can be replicated using PCR. PCR technology is the subject matter of U.S. Pat. Nos. 4,683,195, 4,800,159, 4,754,065, and 4,683,202 and described in PCR: THE POLYMERASE CHAIN REACTION Mullis et al. eds, Birkhauser Press, Boston (1994)) and references cited therein.

Alternatively, one of skill in the art can use the sequences provided herein and a commercial DNA synthesizer to replicate the DNA. Accordingly, this invention also provides a process for obtaining the polynucleotides of this invention by providing the linear sequence of the polynucleotide, appropriate primer molecules, chemicals such as enzymes and instructions for their replication and chemically replicating or linking the nucleotides in the proper orientation to obtain the polynucleotides. In a separate embodiment, these polynucleotides are further isolated. Still further, one of skill in the art can insert the polynucleotide into a suitable replication vector and insert the vector into a suitable host cell (procaryotic or eucaryotic) for replication and amplification. The DNA so amplified can be isolated from the cell by methods well known to those of skill in the art. A process for obtaining polynucleotides by this method is further provided herein as well as the polynucleotides so obtained.

RNA can be obtained by first inserting a DNA polynucleotide into a suitable host cell. The DNA can be inserted by any appropriate method, e.g., by the use of an appropriate gene delivery vehicle (e.g., liposome, plasmid or vector) or by electroporation. When the cell replicates and the DNA is transcribed into RNA; the RNA can then be isolated using methods well known to those of skill in the art, for example, as set forth in Sambrook, et al. (1989) Supra. For instance, mRNA can be isolated using various lytic enzymes or chemical solutions according to the procedures set forth in Sambrook, et al. (1989) Supra or extracted by nucleic-acid-binding resins following the accompanying instructions provided by manufactures.

Polynucleotides having at least 4 contiguous nucleotides, and more preferably at least 5 or 6 contiguous nucleotides and most preferably at least 10 contiguous nucleotides, and exhibiting sequence complementarity or homology to in SEQ ID NOS: 1, 4, 5, and 8 find utility as hybridization probes.

It is known in the art that a "perfectly matched" probe is not needed for a specific hybridization. Minor changes in probe sequence achieved by substitution, deletion or insertion of a small number of bases do not affect the hybridization specificity. In general, as much as 20% base-pair mismatch (when optimally aligned) can be tolerated. Preferably, a probe useful for detecting the aforementioned MRNA is at least about 80% identical to the homologous region of comparable size contained in the previously identified sequences identified as SEQ ID NOS 1, 4, 6, and 8, which correspond to the previously characterized genes in SEQ ID NOS: 1, 5, 7 and 9. More preferably, the probe is 85% identical to the corresponding gene sequence after alignment of the homologous region; even more preferably, it exhibits 90% identity.

These probes can be used in radioassays (e.g. Southern and Northern blot analysis) to detect or monitor various cells or tissue containing these cells. The probes also can be attached to a solid support or an array such as a chip for use in high throughput screening assays for the detection of expression of the gene corresponding to one or more polynucleotide(s) of this invention. Accordingly, this invention also provides at least one probe as defined above of the transcripts identified as SEQ ID NOS: 1, 4, 6, and 8, or the complement of one of these sequences, attached to a solid support for use in high throughput screens.

The polynucleotides of the present invention also can serve as primers for the detection of genes or gene transcripts that are expressed in APC, for example, to confirm transduction of the polynucleotides into host cells. In this context, amplification means any method employing a primer-dependent polymerase capable of replicating a target sequence with reasonable fidelity. Amplification may be carried out by natural or recombinant DNA-polymerases such as T7 DNA polymerase, Klenow fragment of *E.coli* DNA polymerase, and reverse transcriptase. A preferred length of the primer is the same as that identified for probes, above.

The invention further provides the isolated polynucleotide operatively linked to a promoter of RNA transcription, as well as other regulatory sequences for replication and/or transient or stable expression of the DNA or RNA. As used herein, the term "operatively linked" means positioned in such a manner that the promoter will direct transcription of RNA off the DNA molecule. Examples of such promoters are SP6, T4 and T7. In certain embodiments, cell-specific promoters are used for cell-specific expression of the inserted polynucleotide. Vectors which contain a promoter or a promoter/enhancer, with termination codons and selectable marker sequences, as well as a cloning site into which an inserted piece of DNA can be operatively linked to that promoter are well known in the art and commercially available. For general methodology and cloning strategies, see GENE EXPRESSION TECHNOLOGY (Goeddel ed., Academic Press, Inc. (1991)) and references cited therein and VECTORS: ESSENTIAL DATA SERIES (Gacesa and Ramji, eds., John Wiley & Sons, N.Y. (1994)), which contains maps, functional properties, commercial suppliers and a reference to GenEMBL accession numbers for various suitable vectors. Preferable, these vectors are capable of transcribing RNA in vitro or in vivo.

Expression vectors containing these nucleic acids are useful to obtain host vector systems to produce proteins and polypeptides. It is implied that these expression vectors must be replicable in the host organisms either as episomes or as an integral part of the chromosomal DNA. Suitable expression vectors include plasmids, viral vectors, including adenoviruses, adeno-associated viruses, retroviruses, cosmids, etc. Adenoviral vectors are particularly useful for introducing genes into tissues in vivo because of their high levels of expression and efficient transformation of cells both in vitro and in vivo. When a nucleic acid is inserted into a suitable host cell, e.g., a procaryotic or a eucaryotic cell and the host cell replicates, the protein can be recombinantly produced. Suitable host cells will depend on the vector and can include mammalian cells, animal cells, human cells, simian cells, insect cells, yeast cells, and bacterial cells constructed using well known methods. See Sambrook, et al. (1989) Supra. In addition to the use of viral vector for insertion of exogenous nucleic acid into cells, the nucleic acid can be inserted into the host cell by methods well known in the art such as transformation for bacterial cells; transfection using calcium phosphate precipitation for mammalian cells; or DEAE-dextran; electroporation; or microinjection. See Sambrook et al. (1989) Supra for this methodology. Thus, this invention also provides a host cell, e.g. a mammalian cell, an animal cell (rat or mouse), a human cell, or a procaryotic cell such as a bacterial cell, containing a polynucleotide encoding a protein or polypeptide or antibody.

The present invention also provides delivery vehicles suitable for delivery of a polynucleotide of the invention into cells (whether in vivo, ex vivo, or in vitro). A polynucleotide of the invention can be contained within a cloning or expression vector. These vectors (especially expression vectors) can in turn be manipulated to assume any of a number of forms which may, for example, facilitate delivery to and/or entry into a cell.

When the vectors are used for gene therapy in vivo or ex vivo, a pharmaceutically acceptable vector is preferred, such as a replication-incompetent retroviral or adenoviral vector. Pharmaceutically acceptable vectors containing the nucleic acids of this invention can be further modified for transient or stable expression of the inserted polynucleotide. As used herein, the term "pharmaceutically acceptable vector" includes, but is not limited to, a vector or delivery vehicle having the ability to selectively target and introduce the nucleic acid into dividing cells. An example of such a vector is a "replication-incompetent" vector defined by its inability to produce viral proteins, precluding spread of the vector in the infected host cell. An example of a replication-incompetent retroviral vector is LNL6 (Miller, A. D. et al. (1989) BioTechniques 7:980–990). The methodology of using replication-incompetent retroviruses for retroviral-mediated gene transfer of gene markers is well established (Correll, et al. (1989) PNAS USA 86:8912; Bordignon (1989) PNAS USA 86:8912–52; Culver, K. (1991) PNAS USA 88:3155; and Rill, D. R. (1991) Blood 79(10):2694–700.

These host cells containing the polynucleotides of this invention are useful for the recombinant replication of the polynucleotides and for the recombinant production of peptides. Alternatively, the cells may be used to induce an immune response in a subject in the methods described herein. When the host cells are antigen presenting cells, they can be used to expand a population of immune effector cells such as tumor infiltrating lymphocytes which in turn are useful in adoptive immunotherapies.

Also provided by this invention is an antibody capable of specifically forming a complex with the polypeptides of this invention. The term "antibody" includes polyclonal antibodies and monoclonal antibodies. The antibodies include, but are not limited to mouse, rat, and rabbit or human antibodies. The antibodies are useful to identify and purify polypeptides and APCs expressing the polypeptides.

Laboratory methods for producing polyclonal antibodies and monoclonal antibodies, as well as deducing their corresponding nucleic acid sequences, are known in the art, see Harlow and Lane (1988) Supra and Sambrook, et al. (1989) Supra. The monoclonal antibodies of this invention can be biologically produced by introducing protein or a fragment thereof into an animal, e.g., a mouse or a rabbit. The antibody producing cells in the animal are isolated and fused with myeloma cells or heteromyeloma cells to produce hybrid cells or hybridomas. Accordingly, the hybridoma cells producing the monoclonal antibodies of this invention also are provided.

Thus, using the protein or fragment thereof, and well known methods, one of skill in the art can produce and screen the hybridoma cells and antibodies of this invention for antibodies having the ability to bind the proteins or polypeptides.

If a monoclonal antibody being tested binds with the protein or polypeptide, then the antibody being tested and the antibodies provided by the hybridomas of this invention are equivalent. It also is possible to determine without undue experimentation, whether an antibody has the same specificity as the monoclonal antibody of this invention by determining whether the antibody being tested prevents a monoclonal antibody of this invention from binding the protein or polypeptide with which the monoclonal antibody is normally reactive. If the antibody being tested competes with the monoclonal antibody of the invention as shown by a decrease in binding by the monoclonal antibody of this invention, then it is likely that the two antibodies bind to the same or a closely related epitope. Alternatively, one can pre-incubate the monoclonal antibody of this invention with a protein with which it is normally reactive, and determine if the monoclonal antibody being tested is inhibited in its ability to bind the antigen. If the monoclonal antibody being tested is inhibited then, in all likelihood, it has the same, or a closely related, epitopic specificity as the monoclonal antibody of this invention.

The term "antibody" also is intended to include antibodies of all isotypes. Particular isotypes of a monoclonal antibody can be prepared either directly by selecting from the initial fusion, or prepared secondarily, from a parental hybridoma secreting a monoclonal antibody of different isotype by using the sib selection technique to isolate class switch variants using the procedure described in Steplewski, et al. (1985) Proc. Natl. Acad. Sci. 82:8653 or Spira, et al. (1984) J. Immunol. Methods 74:307.

This invention also provides biological active fragments of the polyclonal and monoclonal antibodies described above. These "antibody fragments" retain some ability to selectively bind with its antigen or immunogen. Such antibody fragments can include, but are not limited to:

(1) Fab, (2) Fab', (3) $F(ab')_2$, (4) Fv, and (5) SCA

A specific example of "a biologically active antibody fragment" is a CDR region of the antibody. Methods of making these fragments are known in the art, see for example, Harlow and Lane (1988) Supra.

The antibodies of this invention also can be modified to create chimeric antibodies and humanized antibodies (Oi, et al. (1986) BioTechniques 4(3):214). Chimeric antibodies are those in which the various domains of the antibodies' heavy and light chains are coded for by DNA from more than one species.

The isolation of other hybridomas secreting monoclonal antibodies with the specificity of the monoclonal antibodies of the invention can also be accomplished by one of ordinary skill in the art by producing anti-idiotypic antibodies (Herlyn, et al. (1986) Science 232:100). An anti-idiotypic antibody is an antibody which recognizes unique determinants present on the monoclonal antibody produced by the hybridoma of interest.

Idiotypic identity between monoclonal antibodies of two hybridomas demonstrates that the two monoclonal antibodies are the same with respect to their recognition of the same epitopic determinant. Thus, by using antibodies to the epitopic determinants on a monoclonal antibody it is possible to identify other hybridomas expressing monoclonal antibodies of the same epitopic specificity.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the mirror image of the epitope bound by the first monoclonal antibody. Thus, in this instance, the anti-idiotypic monoclonal antibody could be used for immunization for production of these antibodies.

As used in this invention, the term "epitope" is meant to include any determinant having specific affmity for the monoclonal antibodies of the invention. Epitopic determinants usually consist of chemically active surface groupings of molecules such as amino acids or sugar side chains and usually have specific three dimensional structural characteristics, as well as specific charge characteristics.

The antibodies of this invention can be linked to a detectable agent or label. There are many different labels and methods of labeling known to those of ordinary skill in the art.

The coupling of antibodies to low molecular weight haptens can increase the sensitivity of the assay. The haptens can then be specifically detected by means of a second reaction. For example, it is common to use haptens such as biotin, which reacts avidin, or dinitropherryl, pyridoxal, and fluorescein, which can react with specific anti-hapten antibodies. See Harlow and Lane (1988) supra.

The monoclonal antibodies of the invention also can be bound to many different carriers. Thus, this invention also provides compositions containing the antibodies and another substance, active or inert. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such, using routine experimentation.

Compositions containing the antibodies, fragments thereof or cell lines which produce the antibodies, are encompassed by this invention. When these compositions are to be used pharmaceutically, they are combined with a pharmaceutically acceptable carrier.

In another embodiment the present invention provides a method of inducing an immune response comprising delivering the compounds and compositions of the invention in the context of an MHC molecule. Thus, the polypeptides of this invention can be pulsed into antigen presenting cells using the methods described herein. Antigen-presenting cells, include, but are not limited to dendritic cells (DCs), monocytes/macrophages, B lymphocytes or other cell type (s) expressing the necessary MHC/co-stimulatory molecules. The methods described below focus primarily on DCs which are the most potent, preferred APCs. These host cells containing the polypeptides or proteins are further provided.

Isolated host cells which present the polypeptides of this invention in the context of MHC molecules are further useful to expand and isolate a population of educated, antigen-specific immune effector cells. The immune effector cells, e.g., cytotoxic T lymphocytes, are produced by culturing naive immune effector cells with antigen-presenting cells which present the polypeptides in the context of MHC molecules on the surface of the APCs. The population can be purified using methods known in the art, e.g., FACS analysis or ficoll gradient. The methods to generate and culture the immune effector cells as well as the populations produced thereby also are the inventor's contribution and invention. Pharmaceutical compositions comprising the cells and pharmaceutically acceptable carriers are useful in adoptive immunotherapy. Prior to administration in vivo, the immune effector cells are screened in vitro for their ability to lyse HER2 expressing tumor cells.

In one embodiment, the immune effector cells and/or the APCs are genetically modified. Using standard gene transfer, genes coding for co-stimulatory molecules and/or stimulatory cytokines can be inserted prior to, concurrent to or subsequent to expansion of the immune effector cells.

This invention also provides methods of inducing an immune response in a subject, comprising administering to the subject an effective amount of the polypeptides described above under the conditions that induce an immune response to the polypeptide. The polypeptides can be administered in formulations or as polynucleotides encoding the polypeptides. The polynucleotides can be administered in a gene delivery vehicle or by inserting into a host cell which in turn recombinantly transcribes, translates and processed the encoded polypeptide. Isolated host cells containing the polynucleotides of this invention in a pharmaceutically acceptable carrier can therefore combined with appropriate and effective amount of an adjuvant, cytokine or co-stimulatory molecule for an effective vaccine regimen. In one embodiment, the host cell is an APC such as a dendritic cell. The host cell can be further modified by inserting of a polynucleotide coding for an effective amount of either or both of a cytokine a co-stimulatory molecule.

The methods of this invention can be further modified by co-administering an effective amount of a cytokine or co-stimulatory molecule to the subject.

This invention also provides compositions containing any of the above-mentioned proteins, polypeptides, polynucleotides, vectors, cells, antibodies and fragments thereof, and an acceptable solid or liquid carrier. When the compositions are used pharmaceutically, they are combined with a "pharmaceutically acceptable carrier" for diagnostic and therapeutic use. These compositions also can be used for the preparation of medicaments for the diagnosis and treatment of diseases such as cancer.

The following materials and methods are intended to illustrate, but not limit this invention and to illustrate how to make and use the inventions described above.

Materials and Methods

Production of the Polypeptides of the Invention

Most preferably, isolated peptides of the present invention can be synthesized using an appropriate solid state synthetic procedure. Steward and Young, Solid Phase Peptide Synthesis, Freemantle, San Francisco, Calif. (1968). A preferred method is the Merrifield process. Merrifield, (1967) Recent Progress in Hormone Res. 23:451. The antigenic activity of these peptides may conveniently be tested using, for example, the assays as described herein.

Once an isolated peptide of the invention is obtained, it may be purified by standard methods including chromatography (e.g., ion exchange, affinity, and sizing column chromatography), centrifugation, differential solubility, or by any other standard technique for protein purification. For immunoaffinity chromatography, an epitope may be isolated by binding it to an affinity column comprising antibodies that were raised against that peptide, or a related peptide of the invention, and were affixed to a stationary support.

Alternatively, affinity tags such as hexa-His (Invitrogen), Maltose binding domain (New England Biolabs), influenza coat sequence (Kolodziej, et al. (1991) Methods Enzymol. 194:508–509), and glutathione-S-transferase can be attached to the peptides of the invention to allow easy purification by passage over an appropriate affinity column. Isolated peptides can also be physically characterized using such techniques as proteolysis, nuclear magnetic resonance, and x-ray crystallography.

Also included within the scope of the invention are antigenic peptides that are differentially modified during or after translation, e.g., by phosphorylation, glycosylation, crosslinking, acylation, proteolytic cleavage, linkage to an antibody molecule, membrane molecule or other ligand, (Ferguson, et al. (1988) Ann. Rev. Biochem. 57:285–320).

Isolation, Culturing and Expansion of APCs, Including Dendritic Cells

The following is a brief description of two findamental approaches for the isolation of APC. These approaches involve (1) isolating bone marrow precursor cells ($CD34^+$) from blood and stimulating them to differentiate into APC; or (2) collecting the precommitted APCs from peripheral blood. In the first approach, the patient must be treated with cytokines such as GM-CSF to boost the number of circulating $CD34^+$ stem cells in the peripheral blood.

The second approach for isolating APCs is to collect the relatively large numbers of precommitted APCs already circulating in the blood. Previous techniques for isolating committed APCs from human peripheral blood have involved combinations of physical procedures such as metrizamide gradients and adherence/nonadherence steps (Freudenthal, P.S. et al. (1990) PNAS 87:7698–7702); Percoll gradient separations (Mehta-Damani, et al. (1994) J. Immunol. 153:996–1003); and fluorescence activated cell sorting techniques (Thomas, R. et al. (1993) J. Immunol. 151:6840–52).

One technique for separating large numbers of cells from one another is known as countercurrent centrifugal elutriation (CCE). In this technique, cells are subject to simultaneous centrifugation and a washout stream of buffer which is constantly increasing in flow rate. The constantly increasing countercurrent flow of buffer leads to fractional cell separations that are largely based on cell size.

In one aspect of the invention, the APC are precommitted or mature dendritic cells which can be isolated from the white blood cell fraction of a mammal, such as a murine, simian or a human (See, e.g., WO 96/23060). The white blood cell fraction can be from the peripheral blood of the mammal. This method includes the following steps: (a) providing a white blood cell fraction obtained from a mammalian source by methods known in the art such as leukophoresis; (b) separating the white blood cell fraction of step (a) into four or more subfractions by countercurrent centrifugal elutriation, (c) stimulating conversion of monocytes in one or more fractions from step (b) to dendritic cells by contacting the cells with calcium ionophore, GM-CSF and IL-13 or GM-CSF and IL-4, (d) identifying the dendritic cell-enriched fraction from step (c), and (e) collecting the enriched fraction of step (d), preferably at about 4° C. One way to identify the dendritic cell-enriched fraction is by fluorescence-activated cell sorting. The white blood cell fraction can be treated with calcium ionophore in the presence of other cytokines, such as recombinant (rh) rhIL-12, rhGM-CSF, or rhIL-4. The cells of the white blood cell fraction can be washed in buffer and suspended in $Ca^{++}$/$Mg^{++}$ free media prior to the separating step. The white blood cell fraction can be obtained by leukapheresis. The dendritic cells can be identified by the presence of at least one of the following markers: HLA-DR, HLA-DQ, or B7.2, and the simultaneous absence of the following markers: CD3, CD 14, CD16, 56, 57, and CD 19, 20. Monoclonal antibodies specific to these cell surface markers are commercially available.

More specifically, the method requires collecting an enriched collection of white cells and platelets from leukapheresis that is then further fractionated by countercurrent centrifugal elutriation (CCE) (Abrahamsen, T. G. et al. (1991) J. Clin. Apheresis. 6:48–53). Cell samples are placed in a special elutriation rotor. The rotor is then spun at a constant speed of, for example, 3000 rpm. Once the rotor has reached the desired speed, pressurized air is used to control the flow rate of cells. Cells in the elutriator are subjected to simultaneous centrifugation and a washout stream of buffer which is constantly increasing in flow rate. This results in fractional cell separations based largely but not exclusively on differences in cell size.

Quality control of APC and more specifically DC collection and confirmation of their successful activation in culture is dependent upon a simultaneous multi-color FACS analysis technique which monitors both monocytes and the dendritic cell subpopulation as well as possible contaminant T lymphocytes. It is based upon the fact that DCs do not express the following markers: CD3 (T cell); CD14 (monocyte); CD16, 56, 57 (NK/LAK cells); CD19, 20 (B cells). At the same time, DCs do express large quantities of HLA-DR, significant HLA-DQ and B7.2 (but little or no B7.1) at the time they are circulating in the blood (in addition they express Leu M7 and M9, myeloid markers which are also expressed by monocytes and neutrophils).

When combined with a third color reagent for analysis of dead cells, propridium iodide (PI), it is possible to make positive identification of all cell subpopulations (see Table 1):

TABLE 1

FACS analysis of fresh peripheral cell subpopulations

| | Color#1 Cocktail 3/14/16/19/20/56/57 | Color#2 HLA-DR | Color#3 PI |
|---|---|---|---|
| Live Dendritic cells | Negative | Positive | Negative |
| Live Monocytes | Positive | Positive | Negative |
| Live Neutrophils | Negative | Negative | Negative |
| Dead Cells | Variable | Variable | Positive |

Additional markers can be substituted for additional analysis:

Color #1: CD3 alone, CD14 alone, etc.; Leu M7 or Leu M9; anti-Class I, etc.

Color #2: HLA-Dq, B7.1, B7.2, CD25 (IL2r), ICAM, LFA-3, etc.

The goal of FACS analysis at the time of collection is to confirm that the DCs are enriched in the expected fractions, to monitor neutrophil contamination, and to make sure that appropriate markers are expressed. This rapid bulk collection of enriched DCs from human peripheral blood, suitable for clinical applications, is absolutely dependent on the analytic FACS technique described above for quality control. If need be, mature DCs can be immediately separated from monocytes at this point by fluorescent sorting for "cocktail negative" cells. It may not be necessary to routinely separate DCs from monocytes because, as will be detailed below, the monocytes themselves are still capable of differentiating into DCs or functional DC-like cells in culture.

Once collected, the DC rich/monocyte APC fractions (usually 150 through 190) can be pooled and cryopreserved for future use, or immediately placed in short term culture.

Alternatively, others have reported that a method for upregulating (activating) dendritic cells and converting monocytes to an activated dendritic cell phenotype. This method involves the addition of calcium ionophore to the culture media convert monocytes into activated dendritic cells. Adding the calcium ionophore A23187, for example, at the beginning of a 24–48 hour culture period resulted in uniform activation and dendritic cell phenotypic conversion of the pooled "monocyte plus DC" fractions: characteristically, the activated population becomes uniformly CD14 (Leu M3) negative, and upregulates HLA-DR, HLA-DQ, ICAM-1, B7.1, and B7.2. Furthermore this activated bulk population functions as well on a small numbers basis as a further purified.

Specific combination(s) of cytokines have been used successfully to amplify (or partially substitute) for the activation/conversion achieved with calcium ionophore: these cytokines include but are not limited to purified or recombinant ("rh") rhGM-CSF, rhIL-2, and rhIL-4. Each cytokine when given alone is inadequate for optimal upregulation.

Presentation of Antigen to the APC

For purposes of immunization, the antigenic peptides (Seq. ID Nos. 3, 5 and 7) can be delivered to antigen-presenting cells as protein/peptide or in the form of cDNA encoding the protein/peptide. Antigen-presenting cells (APCs) can consist of dendritic cells (DCs), monocytes/macrophages, B lymphocytes or other cell type(s) expressing the necessary MHC/co-stimulatory molecules. The methods described below focus primarily on DCs which are the most potent, preferred APCs.

Pulsing is accomplished in vitro/ex vivo by exposing APCs to the antigenic protein or peptide(s) of this invention. The protein or peptide(s) are added to APCs at a concentration of 1–10 $\mu$m for approximately 3 hours. Pulsed APCs can subsequently be administered to the host via an intravenous, subcutaneous, intranasal, intramuscular or intraperitoneal route of delivery.

Protein/peptide antigen can also be delivered in vivo with adjuvant via the intravenous, subcutaneous, intranasal, intramuscular or intraperitoneal route of delivery.

Paglia, et al. (1996) J. Exp. Med. 183:317–322 has shown that APC incubated with whole protein in vitro were recognized by MHC class I-restricted CTLs, and that immunization of animals with these APCs led to the development of antigen-specific CTLs in vivo. In addition, several different techniques have been described which lead to the expression of antigen in the cytosol of APCs, such as DCs. These include (1) the introduction into the APCs of RNA isolated from tumor cells, (2) infection of APCs with recombinant vectors to induce endogenous expression of antigen, and (3) introduction of tumor antigen into the DC cytosol using liposomes. (See Boczkowski, D. et al. (1996) J. Exp. Med. 184:465–472; Rouse, et al. (1994) J. Virol. 68:5685–5689; and Nair, et al. (1992) J. Exp. Med. 175:609–612).

Foster Antigen Presenting Cells

Foster antigen presenting cells are particularly useful as target. Foster APCs are derived from the human cell line 174×CEM.T2, referred to as T2, which contains a mutation in its antigen processing pathway that restricts the association of endogenous peptides with cell surface MHC class I molecules (Zweerink, et al. (1993) *J Immunol.* 150:1763–1771). This is due to a large homozygous deletion in the MHC class II region encompassing the genes TAP1, TAP2, LMP1, and LMP2, which are required for antigen presentation to MHC class 1 -restricted $CD8^+$ CTLs. In effect, only "empty" MHC class I molecules are presented on the surface of these cells. Exogenous peptide added to the culture medium binds to these MHC molecules provided that the peptide contains the allele-specific binding motif. These T2 cells are referred to herein as "foster" APCs. They can be used in conjunction with this invention to present antigen(s).

Transduction of T2 cells with specific recombinant MHC alleles allows for redirection of the MHC restriction profile. Libraries tailored to the recombinant allele will be preferentially presented by them because the anchor residues will prevent efficient binding to the endogenous allele.

High level expression of MHC molecules makes the APC more visible to the CTLs. Expressing the MHC allele of interest in T2 cells using a powerful transcriptional promoter (e.g., the CMV promoter) results in a more reactive APC (most likely due to a higher concentration of reactive MHC-peptide complexes on the cell surface).

Expansion of Immune Effector Cells

The present invention makes use of these APCs to stimulate production of an enriched population of antigen-specific immune effector cells. The antigen-specific immune effector cells are expanded at the expense of the APCs, which die in the culture. The process by which naïve immune effector cells become educated by other cells is described essentially in Coulie (1997) Molec. Med. Today 3:261–268.

The APCs prepared as described above are mixed with naïve immune effector cells. Preferably, the cells may be cultured in the presence of a cytokine, for example IL2. Because dendritic cells secrete potent immunostimulatory cytokines, such as IL12, it may not be necessary to add supplemental cytokines during the first and successive rounds of expansion. In any event, the culture conditions are such that the antigen-specific immune effector cells expand (i.e. proliferate) at a much higher rate than the APCs. Multiple infusions of APCs and optional cytokines can be performed to further expand the population of antigen-specific cells.

In one embodiment, the immune effector cells are T cells. In a separate embodiment, the immune effector cells can be genetically modified by transduction with a transgene coding for example, IL-2, IL-11 or IL-13. Methods for introducing transgenes in vitro, ex vivo and in vivo are well known in the art. See Sambrook, et al. (1989) Supra.

Vectors Useful in Genetic Modifications

In general, genetic modifications of cells employed in the present invention are accomplished by introducing a vector containing a polypeptide or transgene encoding a heterologous or an altered antigen. A variety of different gene transfer vectors, including viral as well as non-viral systems can be used. Viral vectors useful in the genetic modifications of this invention include, but are not limited to adenovirus, adeno-associated virus vectors, retroviral vectors and adeno-retroviral chimeric vectors. APC and immune effector cells can be modified using the methods described below or by any other appropriate method known in the art.

Construction of Recombinant Adenoviral Vectors or Adeno-Associated Virus Vectors Adenovirus and adeno-associated virus vectors useful in the genetic modifications of this invention may be produced according to methods already taught in the art. (see, e.g., Karlsson, et al. (1986) EMBO 5:2377; Carter (1992) Current Opinion in Biotechnology 3:533–539; Muzcyzka (1992) Current Top. Microbiol. Immunol. 158:97–129; GENE TARGETING: A PRACTICAL APPROACH (1992) ed. A. L. Joyner, Oxford University Press, N.Y.). Several different approaches are feasible. Preferred is the helper-independent replication deficient human adenovirus system.

The recombinant adenoviral vectors based on the human adenovirus 5 (Virology 163:614–617 (1988)) are missing essential early genes from the adenoviral genome (usually E1A/E1B), and are therefore unable to replicate unless grown in permissive cell lines that provide the missing gene products in trans. In place of the missing adenoviral genomic sequences, a transgene of interest can be cloned and expressed in cells infected with the replication deficient adenovirus. Although adenovirus-based gene transfer does not result in integration of the transgene into the host genome (less than 0.1% adenovirus-mediated transfections result in transgene incorporation into host DNA), and therefore is not stable, adenoviral vectors can be propagated in high titer and transfect non-replicating cells. Human 293 cells, which are human embryonic kidney cells transformed with adenovirus E1A/E1B genes, typify useful permissive cell lines. However, other cell lines which allow replication-deficient adenoviral vectors to propagate therein can be used, including HeLa cells.

Additional references describing adenovirus vectors and other viral vectors which could be used in the methods of the present invention include the following: Horwitz, M. S., Adenoviridae and Their Replication, in Fields, B., et al. (eds.) VIROLOGY, Vol. 2, Raven Press New York, pp. 1679–1721, 1990); Graham, F. et al., pp. 109–128 in METHODS IN MOLECULAR BIOLOGY, Vol. 7: GENE TRANSFER AND EXPRESSION PROTOCOLS, Murray, E. (ed.), Humana Press, Clifton, N.J. (1991); Miller, N., et al. (1995) FASEB Journal 9:190–199 Schreier, H (1994) Pharmaceutica Acta Helvetiae 68:145–159; Schneider and French (1993) Circulation 88:1937–1942; Curiel D. T., et al.(1992) Human Gene Therapy 3:147–154; Graham, F. L., et al., WO 95/00655 (Jan. 5, 1995); Falck-Pedersen, E. S. WO 95/16772 (Jun. 22, 1995); Denefle, P. et al. WO 95/23867 (Sep. 8, 1995); Haddada, H. et al. WO 94/26914 (Nov. 24, 1994); Perricaudet, M. et al. WO 95/02697 (Jan. 26, 1995); Zhang, W. et al. WO 95/25071 (Oct. 12, 1995). A variety of adenovirus plasmids are also available from commercial sources, including, e.g., Microbix Biosystems of Toronto, Ontario (see, e.g., Microbix Product Information Sheet: Plasmids for Adenovirus Vector Construction, 1996). See also, the papers by Vile, et al. (1997) Nature Biotechnology 15:840–841; Feng, et al.(1997) Nature Biotechnology, 15:866–870, describing the construction and use of adeno-retroviral chimeric vectors that can be employed for genetic modifications.

Additional references describing AAV vectors which could be used in the methods of the present invention include the following: Carter, B., HANDBOOK OF PARVOVIRUSES, Vol. I, pp. 169–228, 1990; Bems, VIROLOGY, pp. 1743–1764 (Raven Press 1990); Carter, B. (1992) Curr. Opin. Biotechnol. 3:533–539; Muzyczka, N. (1992) Current Topics in Micro and Immunol, 158:92–129; Flotte, T. R. et al. (1992) Am. J. Respir. Cell Mol. Biol. 7:349–356; Chatterjee, et al. (1995) Ann. NY Acad. Sci. 770:79–90; Flotte, T. R. et al. WO 95/13365 (May 18, 1995); Trempe, J. P. et al., WO 95/13392 (May 18, 1995); Kotin, R.(1994) Human Gene Therapy 5:793–801; Flotte, T. R. et al. (1995) Gene Therapy 2:357–362; Allen, J. M., WO 96/17947 (Jun. 13, 1996); and Du, et al. (1996) Gene Therapy 3:254–261.

APCs can be transduced with viral vectors encoding a relevant polypeptides. The most common viral vectors include recombinant poxviruses such as vaccinia and fowlpox virus (Bronte, et al. (1997) PNAS 94:3183–3188; Kim, et al. (1997) J. Immunother. 20:276–286) and, preferentially, adenovirus (Arthur, et al. (1997) J. Immunol. 159:1393–1403; Wan, et al. (1997) Human Gene Therapy 8:1355–1363; Huang, et al. (1995) J. Virol. 69:2257–2263). Retrovirus also may be used for transduction of human APCs (Marin, et al. (1996) J. Virol. 70:2957–2962).

In vitro/ex vivo, exposure of human DCs to adenovirus (Ad) vector at a multiplicity of infection (MOI) of 500 for 16–24 h in a minimal volume of serum-free medium reliably gives rise to transgene expression in 90–100% of DCs. The efficiency of transduction of DCs or other APCs can be assessed by immunofluorescence using fluorescent antibodies specific for the tumor antigen being expressed (Kim, et al. (1997) J. Immunother. 20:276–286). Alternatively, the antibodies can be conjugated to an enzyme (e.g. HRP) giving rise to a colored product upon reaction with the substrate. The actual amount of antigenic polypeptides being expressed by the APCs can be evaluated by ELISA.

Transduced APCs can subsequently be administered to the host via an intravenous, subcutaneous, intranasal, intramuscular or intraperitoneal route of delivery.

In vivo transduction of DCs, or other APCs, can be accomplished by administration of Ad (or other viral vectors) via different routes including intravenous, intramuscular, intranasal, intraperitoneal or cutaneous delivery. The preferred method is cutaneous delivery of Ad vector at multiple sites using a total dose of approximately $1\times10^{10}$–$1\times10^{12}$ i.u. Levels of in vivo transduction can be roughly assessed by co-staining with antibodies directed against APC marker(s) and the TAA being expressed. The staining procedure can be carried out on biopsy samples from the site of administration or on cells from draining lymph nodes or other organs where APCs (in particular DCs) may have migrated (Condon, et al. (1996) Nature Med. 2:1122–1128; Wan, et al. (1997) Human Gene Therapy 8:1355–1363). The amount of antigen being expressed at the site of injection or in other organs where transduced APCs may have migrated can be evaluated by ELISA on tissue homogenates.

Although viral gene delivery is more efficient, DCs can also be transduced in vitro/ex vivo by non-viral gene delivery methods such as electroporation, calcium phosphate precipitation or cationic lipid/plasmid DNA complexes (Arthur, et al. (1997) Cancer Gene Therapy 4:17–25). Transduced APCs can subsequently be administered to the host via an intravenous, subcutaneous, intranasal, intramuscular or intraperitoneal route of delivery.

In vivo transduction of DCs, or other APCs, can potentially be accomplished by administration of cationic lipid/plasmid DNA complexes delivered via the intravenous, intramuscular, intranasal, intraperitoneal or cutaneous route of administration. Gene gun delivery or injection of naked plasmid DNA into the skin also leads to transduction of DCs (Condon, et al. (1996) Nature Med. 2:1122–1128; Raz, et al (1994) PNAS 91:9519–9523). Intramuscular delivery of plasmid DNA may also be used for immunization (Rosato, et al. (1997) Human Gene Therapy 8:1451–1458.

The transduction efficiency and levels of transgene expression can be assessed as described above for viral vectors.

Adoptive Immunotherapy and Vaccines

The expanded populations of antigen-specific immune effector cells of the present invention also find use in adoptive immunotherapy regimes and as vaccines.

Adoptive immunotherapy methods involve, in one aspect, administering to a subject a substantially pure population of educated, antigen-specific immune effector cells made by culturing naïve immune effector cells with APCs as described above. Preferably, the APCs are dendritic cells.

In one embodiment, the adoptive immunotherapy methods described herein are autologous. In this case, the APCs are made using parental cells isolated from a single subject. The expanded population also employs T cells isolated from that subject. Finally, the expanded population of antigen-specific cells is administered to the same patient.

In a further embodiment, APCs or immune effector cells are administered with an effective amount of a stimulatory cytokine, such as IL-2 or a co-stimulatory molecule.

The agents identified herein as effective for their intended purpose can be administered to subjects having tumors expressing HER2 or to individuals susceptible to or at risk of developing such tumors. When the agent is administered to a subject such as a mouse, a rat or a human patient, the agent can be added to a pharmaceutically acceptable carrier and systemically or topically administered to the subject. To determine patients that can be beneficially treated, a tumor regression can be assayed. Therapeutic amounts can be empirically determined and will vary with the pathology being treated, the subject being treated and the efficacy and toxicity of the therapy.

Administration in vivo can be effected in one dose, continuously or intermittently throughout the course of treatment. Methods of determining the most effective means and dosage of administration are well known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents can be found below.

The agents and compositions of the present invention can be used in the manufacture of medicaments and for the treatment of humans and other animals by administration in accordance with conventional procedures, such as an active ingredient in pharmaceutical compositions.

More particularly, an agent of the present invention also referred to herein as the active ingredient, may be administered for therapy by any suitable route including nasal, topical (including transdermal, aerosol, buccal and sublingual), parental (including subcutaneous, intramuscular, intravenous and intradermal) and pulmonary. It will also be appreciated that the preferred route will vary with the condition and age of the recipient, and the disease being treated.

The preceding discussion and examples are intended merely to illustrate the art. As is apparent to one of skill in the art, various modifications can be made to the above without departing from the spirit and scope of this invention.

What is claimed is:
1. A compound of the structure:
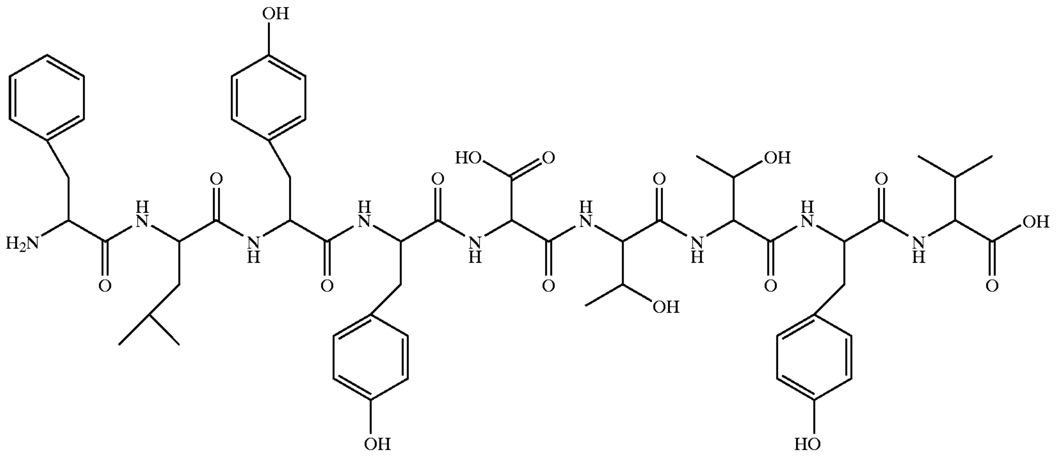
2. A peptide consisting of the amino acid sequence of SEQ ID NO: 3.
* * * * *

SEQUENCE LISTING

```
<160> NUMBER OF SEQ ID NOS: 9

<210> SEQ ID NO 1
<211> LENGTH: 4530
<212> TYPE: DNA
<213> ORGANISM: Homo sapiens
<220> FEATURE:
<221> NAME/KEY: CDS
<222> LOCATION: (151)..(3915)

<400> SEQUENCE: 1

aattctcgag ctcgtcgacc ggtcgacgag ctcgagggtc gacgagctcg agggcgcgcg      60

cccggccccc acccctcgca gcaccccgcg ccccgcgccc tcccagccgg gtccagccgg     120

agccatgggg ccggagccgc agtgagcacc atg gag ctg gcg gcc ttg tgc cgc      174
                                 Met Glu Leu Ala Ala Leu Cys Arg
                                   1               5

tgg ggg ctc ctc ctc gcc ctc ttg ccc ccc gga gcc gcg agc acc caa      222
Trp Gly Leu Leu Leu Ala Leu Leu Pro Pro Gly Ala Ala Ser Thr Gln
```

-continued

```
     10                  15                  20

gtg tgc acc ggc aca gac atg aag ctg cgg ctc cct gcc agt ccc gag       270
Val Cys Thr Gly Thr Asp Met Lys Leu Arg Leu Pro Ala Ser Pro Glu
 25                  30                  35                  40

acc cac ctg gac atg ctc cgc cac ctc tac cag ggc tgc cag gtg gtg       318
Thr His Leu Asp Met Leu Arg His Leu Tyr Gln Gly Cys Gln Val Val
                 45                  50                  55

cag gga aac ctg gaa ctc acc tac ctg ccc acc aat gcc agc ctg tcc       366
Gln Gly Asn Leu Glu Leu Thr Tyr Leu Pro Thr Asn Ala Ser Leu Ser
             60                  65                  70

ttc ctg cag gat atc cag gag gtg cag ggc tac gtg ctc atc gct cac       414
Phe Leu Gln Asp Ile Gln Glu Val Gln Gly Tyr Val Leu Ile Ala His
         75                  80                  85

aac caa gtg agg cag gtc cca ctg cag agg ctg cgg att gtg cga ggc       462
Asn Gln Val Arg Gln Val Pro Leu Gln Arg Leu Arg Ile Val Arg Gly
     90                  95                 100

acc cag ctc ttt gag gac aac tat gcc ctg gcc gtg cta gac aat gga       510
Thr Gln Leu Phe Glu Asp Asn Tyr Ala Leu Ala Val Leu Asp Asn Gly
105                 110                 115                 120

gac ccg ctg aac aat acc acc cct gtc aca ggg gcc tcc cca gga ggc       558
Asp Pro Leu Asn Asn Thr Thr Pro Val Thr Gly Ala Ser Pro Gly Gly
                125                 130                 135

ctg cgg gag ctg cag ctt cga agc ctc aca gag atc ttg aaa gga ggg       606
Leu Arg Glu Leu Gln Leu Arg Ser Leu Thr Glu Ile Leu Lys Gly Gly
            140                 145                 150

gtc ttg atc cag cgg aac ccc cag ctc tgc tac cag gac acg att ttg       654
Val Leu Ile Gln Arg Asn Pro Gln Leu Cys Tyr Gln Asp Thr Ile Leu
        155                 160                 165

tgg aag gac atc ttc cac aag aac aac cag ctg gct ctc aca ctg ata       702
Trp Lys Asp Ile Phe His Lys Asn Asn Gln Leu Ala Leu Thr Leu Ile
    170                 175                 180

gac acc aac cgc tct cgg gcc tgc cac ccc tgt tct ccg atg tgt aag       750
Asp Thr Asn Arg Ser Arg Ala Cys His Pro Cys Ser Pro Met Cys Lys
185                 190                 195                 200

ggc tcc cgc tgc tgg gga gag agt tct gag gat tgt cag agc ctg acg       798
Gly Ser Arg Cys Trp Gly Glu Ser Ser Glu Asp Cys Gln Ser Leu Thr
                205                 210                 215

cgc act gtc tgt gcc ggt ggc tgt gcc cgc tgc aag ggg cca ctg ccc       846
Arg Thr Val Cys Ala Gly Gly Cys Ala Arg Cys Lys Gly Pro Leu Pro
            220                 225                 230

act gac tgc tgc cat gag cag tgt gct gcc ggc tgc acg ggc ccc aag       894
Thr Asp Cys Cys His Glu Gln Cys Ala Ala Gly Cys Thr Gly Pro Lys
        235                 240                 245

cac tct gac tgc ctg gcc tgc ctc cac ttc aac cac agt ggc atc tgt       942
His Ser Asp Cys Leu Ala Cys Leu His Phe Asn His Ser Gly Ile Cys
    250                 255                 260

gag ctg cac tgc cca gcc ctg gtc acc tac aac aca gac acg ttt gag       990
Glu Leu His Cys Pro Ala Leu Val Thr Tyr Asn Thr Asp Thr Phe Glu
265                 270                 275                 280

tcc atg ccc aat ccc gag ggc cgg tat aca ttc ggc gcc agc tgt gtg      1038
Ser Met Pro Asn Pro Glu Gly Arg Tyr Thr Phe Gly Ala Ser Cys Val
                285                 290                 295

act gcc tgt ccc tac aac tac ctt tct acg gac gtg gga tcc tgc acc      1086
Thr Ala Cys Pro Tyr Asn Tyr Leu Ser Thr Asp Val Gly Ser Cys Thr
            300                 305                 310

ctc gtc tgc ccc ctg cac aac caa gag gtg aca gca gag gat gga aca      1134
Leu Val Cys Pro Leu His Asn Gln Glu Val Thr Ala Glu Asp Gly Thr
        315                 320                 325

cag cgg tgt gag aag tgc agc aag ccc tgt gcc cga gtg tgc tat ggt      1182
```

-continued

```
Gln Arg Cys Glu Lys Cys Ser Lys Pro Cys Ala Arg Val Cys Tyr Gly
    330                 335                 340

ctg ggc atg gag cac ttg cga gag gtg agg gca gtt acc agt gcc aat      1230
Leu Gly Met Glu His Leu Arg Glu Val Arg Ala Val Thr Ser Ala Asn
345                 350                 355                 360

atc cag gag ttt gct ggc tgc aag aag atc ttt ggg agc ctg gca ttt      1278
Ile Gln Glu Phe Ala Gly Cys Lys Lys Ile Phe Gly Ser Leu Ala Phe
                365                 370                 375

ctg ccg gag agc ttt gat ggg gac cca gcc tcc aac act gcc ccg ctc      1326
Leu Pro Glu Ser Phe Asp Gly Asp Pro Ala Ser Asn Thr Ala Pro Leu
            380                 385                 390

cag cca gag cag ctc caa gtg ttt gag act ctg gaa gag atc aca ggt      1374
Gln Pro Glu Gln Leu Gln Val Phe Glu Thr Leu Glu Glu Ile Thr Gly
        395                 400                 405

tac cta tac atc tca gca tgg ccg gac agc ctg cct gac ctc agc gtc      1422
Tyr Leu Tyr Ile Ser Ala Trp Pro Asp Ser Leu Pro Asp Leu Ser Val
    410                 415                 420

ttc cag aac ctg caa gta atc cgg gga cga att ctg cac aat ggc gcc      1470
Phe Gln Asn Leu Gln Val Ile Arg Gly Arg Ile Leu His Asn Gly Ala
425                 430                 435                 440

tac tcg ctg acc ctg caa ggg ctg ggc atc agc tgg ctg ggg ctg cgc      1518
Tyr Ser Leu Thr Leu Gln Gly Leu Gly Ile Ser Trp Leu Gly Leu Arg
                445                 450                 455

tca ctg agg gaa ctg ggc agt gga ctg gcc ctc atc cac cat aac acc      1566
Ser Leu Arg Glu Leu Gly Ser Gly Leu Ala Leu Ile His His Asn Thr
            460                 465                 470

cac ctc tgc ttc gtg cac acg gtg ccc tgg gac cag ctc ttt cgg aac      1614
His Leu Cys Phe Val His Thr Val Pro Trp Asp Gln Leu Phe Arg Asn
        475                 480                 485

ccg cac caa gct ctg ctc cac act gcc aac cgg cca gag gac gag tgt      1662
Pro His Gln Ala Leu Leu His Thr Ala Asn Arg Pro Glu Asp Glu Cys
    490                 495                 500

gtg ggc gag ggc ctg gcc tgc cac cag ctg tgc gcc cga ggg cac tgc      1710
Val Gly Glu Gly Leu Ala Cys His Gln Leu Cys Ala Arg Gly His Cys
505                 510                 515                 520

tgg ggt cca ggg ccc acc cag tgt gtc aac tgc agc cag ttc ctt cgg      1758
Trp Gly Pro Gly Pro Thr Gln Cys Val Asn Cys Ser Gln Phe Leu Arg
                525                 530                 535

ggc cag gag tgc gtg gag gaa tgc cga gta ctg cag ggg ctc ccc agg      1806
Gly Gln Glu Cys Val Glu Glu Cys Arg Val Leu Gln Gly Leu Pro Arg
            540                 545                 550

gag tat gtg aat gcc agg cac tgt ttg ccg tgc cac cct gag tgt cag      1854
Glu Tyr Val Asn Ala Arg His Cys Leu Pro Cys His Pro Glu Cys Gln
        555                 560                 565

ccc cag aat ggc tca gtg acc tgt ttt gga ccg gag gct gac cag tgt      1902
Pro Gln Asn Gly Ser Val Thr Cys Phe Gly Pro Glu Ala Asp Gln Cys
    570                 575                 580

gtg gcc tgt gcc cac tat aag gac cct ccc ttc tgc gtg gcc cgc tgc      1950
Val Ala Cys Ala His Tyr Lys Asp Pro Pro Phe Cys Val Ala Arg Cys
585                 590                 595                 600

ccc agc ggt gtg aaa cct gac ctc tcc tac atg ccc atc tgg aag ttt      1998
Pro Ser Gly Val Lys Pro Asp Leu Ser Tyr Met Pro Ile Trp Lys Phe
                605                 610                 615

cca gat gag gag ggc gca tgc cag cct tgc ccc atc aac tgc acc cac      2046
Pro Asp Glu Glu Gly Ala Cys Gln Pro Cys Pro Ile Asn Cys Thr His
            620                 625                 630

tcc tgt gtg gac ctg gat gac aag ggc tgc ccc gcc gag cag aga gcc      2094
Ser Cys Val Asp Leu Asp Asp Lys Gly Cys Pro Ala Glu Gln Arg Ala
        635                 640                 645
```

-continued

```
agc cct ctg acg tcc atc gtc tct gcg gtg gtt ggc att ctg ctg gtc     2142
Ser Pro Leu Thr Ser Ile Val Ser Ala Val Val Gly Ile Leu Leu Val
    650                 655                 660

gtg gtc ttg ggg gtg gtc ttt ggg atc ctc atc aag cga cgg cag cag     2190
Val Val Leu Gly Val Val Phe Gly Ile Leu Ile Lys Arg Arg Gln Gln
665                 670                 675                 680

aag atc cgg aag tac acg atg cgg aga ctg ctg cag gaa acg gag ctg     2238
Lys Ile Arg Lys Tyr Thr Met Arg Arg Leu Leu Gln Glu Thr Glu Leu
                685                 690                 695

gtg gag ccg ctg aca cct agc gga gcg atg ccc aac cag gcg cag atg     2286
Val Glu Pro Leu Thr Pro Ser Gly Ala Met Pro Asn Gln Ala Gln Met
            700                 705                 710

cgg atc ctg aaa gag acg gag ctg agg aag gtg aag gtg ctt gga tct     2334
Arg Ile Leu Lys Glu Thr Glu Leu Arg Lys Val Lys Val Leu Gly Ser
        715                 720                 725

ggc gct ttt ggc aca gtc tac aag ggc atc tgg atc cct gat ggg gag     2382
Gly Ala Phe Gly Thr Val Tyr Lys Gly Ile Trp Ile Pro Asp Gly Glu
    730                 735                 740

aat gtg aaa att cca gtg gcc atc aaa gtg ttg agg gaa aac aca tcc     2430
Asn Val Lys Ile Pro Val Ala Ile Lys Val Leu Arg Glu Asn Thr Ser
745                 750                 755                 760

ccc aaa gcc aac aaa gaa atc tta gac gaa gca tac gtg atg gct ggt     2478
Pro Lys Ala Asn Lys Glu Ile Leu Asp Glu Ala Tyr Val Met Ala Gly
                765                 770                 775

gtg ggc tcc cca tat gtc tcc cgc ctt ctg ggc atc tgc ctg aca tcc     2526
Val Gly Ser Pro Tyr Val Ser Arg Leu Leu Gly Ile Cys Leu Thr Ser
            780                 785                 790

acg gtg cag ctg gtg aca cag ctt atg ccc tat ggc tgc ctc tta gac     2574
Thr Val Gln Leu Val Thr Gln Leu Met Pro Tyr Gly Cys Leu Leu Asp
        795                 800                 805

cat gtc cgg gaa aac cgc gga cgc ctg ggc tcc cag gac ctg ctg aac     2622
His Val Arg Glu Asn Arg Gly Arg Leu Gly Ser Gln Asp Leu Leu Asn
    810                 815                 820

tgg tgt atg cag att gcc aag ggg atg agc tac ctg gag gat gtg cgg     2670
Trp Cys Met Gln Ile Ala Lys Gly Met Ser Tyr Leu Glu Asp Val Arg
825                 830                 835                 840

ctc gta cac agg gac ttg gcc gct cgg aac gtg ctg gtc aag agt ccc     2718
Leu Val His Arg Asp Leu Ala Ala Arg Asn Val Leu Val Lys Ser Pro
                845                 850                 855

aac cat gtc aaa att aca gac ttc ggg ctg gct cgg ctg ctg gac att     2766
Asn His Val Lys Ile Thr Asp Phe Gly Leu Ala Arg Leu Leu Asp Ile
            860                 865                 870

gac gag aca gag tac cat gca gat ggg ggc aag gtg ccc atc aag tgg     2814
Asp Glu Thr Glu Tyr His Ala Asp Gly Gly Lys Val Pro Ile Lys Trp
        875                 880                 885

atg gcg ctg gag tcc att ctc cgc cgg cgg ttc acc cac cag agt gat     2862
Met Ala Leu Glu Ser Ile Leu Arg Arg Arg Phe Thr His Gln Ser Asp
    890                 895                 900

gtg tgg agt tat ggt gtg act gtg tgg gag ctg atg act ttt ggg gcc     2910
Val Trp Ser Tyr Gly Val Thr Val Trp Glu Leu Met Thr Phe Gly Ala
905                 910                 915                 920

aaa cct tac gat ggg atc cca gcc cgg gag atc cct gac ctg ctg gaa     2958
Lys Pro Tyr Asp Gly Ile Pro Ala Arg Glu Ile Pro Asp Leu Leu Glu
                925                 930                 935

aag ggg gag cgg ctg ccc cag ccc ccc atc tgc acc att gat gtc tac     3006
Lys Gly Glu Arg Leu Pro Gln Pro Pro Ile Cys Thr Ile Asp Val Tyr
            940                 945                 950

atg atc atg gtc aaa tgt tgg atg att gac tct gaa tgt cgg cca aga     3054
Met Ile Met Val Lys Cys Trp Met Ile Asp Ser Glu Cys Arg Pro Arg
        955                 960                 965
```

-continued

```
ttc cgg gag ttg gtg tct gaa ttc tcc cgc atg gcc agg gac ccc cag      3102
Phe Arg Glu Leu Val Ser Glu Phe Ser Arg Met Ala Arg Asp Pro Gln
    970                 975                 980

cgc ttt gtg gtc atc cag aat gag gac ttg ggc cca gcc agt ccc ttg      3150
Arg Phe Val Val Ile Gln Asn Glu Asp Leu Gly Pro Ala Ser Pro Leu
985                 990                 995                 1000

gac agc acc ttc tac cgc tca ctg ctg gag gac gat gac atg ggg gac      3198
Asp Ser Thr Phe Tyr Arg Ser Leu Leu Glu Asp Asp Asp Met Gly Asp
               1005                1010                1015

ctg gtg gat gct gag gag tat ctg gta ccc cag cag ggc ttc ttc tgt      3246
Leu Val Asp Ala Glu Glu Tyr Leu Val Pro Gln Gln Gly Phe Phe Cys
           1020                1025                1030

cca gac cct gcc ccg ggc gct ggg ggc atg gtc cac cac agg cac cgc      3294
Pro Asp Pro Ala Pro Gly Ala Gly Gly Met Val His His Arg His Arg
       1035                1040                1045

agc tca tct acc agg agt ggc ggt ggg gac ctg aca cta ggg ctg gag      3342
Ser Ser Ser Thr Arg Ser Gly Gly Gly Asp Leu Thr Leu Gly Leu Glu
   1050                1055                1060

ccc tct gaa gag gag gcc ccc agg tct cca ctg gca ccc tcc gaa ggg      3390
Pro Ser Glu Glu Glu Ala Pro Arg Ser Pro Leu Ala Pro Ser Glu Gly
1065               1070                1075                1080

gct ggc tcc gat gta ttt gat ggt gac ctg gga atg ggg gca gcc aag      3438
Ala Gly Ser Asp Val Phe Asp Gly Asp Leu Gly Met Gly Ala Ala Lys
               1085                1090                1095

ggg ctg caa agc ctc ccc aca cat gac ccc agc cct cta cag cgg tac      3486
Gly Leu Gln Ser Leu Pro Thr His Asp Pro Ser Pro Leu Gln Arg Tyr
           1100                1105                1110

agt gag gac ccc aca gta ccc ctg ccc tct gag act gat ggc tac gtt      3534
Ser Glu Asp Pro Thr Val Pro Leu Pro Ser Glu Thr Asp Gly Tyr Val
       1115                1120                1125

gcc ccc ctg acc tgc agc ccc cag cct gaa tat gtg aac cag cca gat      3582
Ala Pro Leu Thr Cys Ser Pro Gln Pro Glu Tyr Val Asn Gln Pro Asp
   1130                1135                1140

gtt cgg ccc cag ccc cct tcg ccc cga gag ggc cct ctg cct gct gcc      3630
Val Arg Pro Gln Pro Pro Ser Pro Arg Glu Gly Pro Leu Pro Ala Ala
1145               1150                1155                1160

cga cct gct ggt gcc act ctg gaa agg gcc aag act ctc tcc cca ggg      3678
Arg Pro Ala Gly Ala Thr Leu Glu Arg Ala Lys Thr Leu Ser Pro Gly
               1165                1170                1175

aag aat ggg gtc gtc aaa gac gtt ttt gcc ttt ggg ggt gcc gtg gag      3726
Lys Asn Gly Val Val Lys Asp Val Phe Ala Phe Gly Gly Ala Val Glu
           1180                1185                1190

aac ccc gag tac ttg aca ccc cag gga gga gct gcc cct cag ccc cac      3774
Asn Pro Glu Tyr Leu Thr Pro Gln Gly Gly Ala Ala Pro Gln Pro His
       1195                1200                1205

cct cct cct gcc ttc agc cca gcc ttc gac aac ctc tat tac tgg gac      3822
Pro Pro Pro Ala Phe Ser Pro Ala Phe Asp Asn Leu Tyr Tyr Trp Asp
   1210                1215                1220

cag gac cca cca gag cgg ggg gct cca ccc agc acc ttc aaa ggg aca      3870
Gln Asp Pro Pro Glu Arg Gly Ala Pro Pro Ser Thr Phe Lys Gly Thr
1225               1230                1235                1240

cct acg gca gag aac cca gag tac ctg ggt ctg gac gtg cca gtg          3915
Pro Thr Ala Glu Asn Pro Glu Tyr Leu Gly Leu Asp Val Pro Val
               1245                1250                1255

tgaaccagaa ggccaagtcc gcagaagccc tgatgtgtcc tcagggagca gggaaggcct   3975

gacttctgct ggcatcaaga ggtgggaggg ccctccgacc acttccaggg gaacctgcca   4035

tgccaggaac ctgtcctaag gaaccttcct tcctgcttga gttcccagat ggctggaagg   4095
```

-continued ggtccagcct cgttggaaga ggaacagcac tggggagtct ttgtggattc tgaggccctg 4155 cccaatgaga ctctagggtc cagtggatgc cacagcccag cttggccctt tccttccaga 4215 tcctgggtac tgaaagcctt agggaagctg gcctgagagg ggaagcggcc ctaagggagt 4275 gtctaagaac aaaagcgacc cattcagaga ctgtccctga aacctagtac tgccccccat 4335 gaggaaggaa cagcaatggt gtcagtatcc aggctttgta cagagtgctt ttctgtttag 4395 tttttacttt ttttgttttg tttttttaaa gacgaaataa agacccaggg gagaatgggt 4455 gttgtatggg gaggcaagtg tgggggtcc ttctccacac ccactttgtc catttgcaaa 4515 tatattttgg aaaac 4530

<210> SEQ ID NO 2
<211> LENGTH: 1255
<212> TYPE: PRT
<213> ORGANISM: Homo sapiens

<400> SEQUENCE: 2

Met Glu Leu Ala Ala Leu Cys Arg Trp Gly Leu Leu Leu Ala Leu Leu
1 5 10 15

Pro Pro Gly Ala Ala Ser Thr Gln Val Cys Thr Gly Thr Asp Met Lys
20 25 30

Leu Arg Leu Pro Ala Ser Pro Glu Thr His Leu Asp Met Leu Arg His
35 40 45

Leu Tyr Gln Gly Cys Gln Val Val Gln Gly Asn Leu Glu Leu Thr Tyr
50 55 60

Leu Pro Thr Asn Ala Ser Leu Ser Phe Leu Gln Asp Ile Gln Glu Val
65 70 75 80

Gln Gly Tyr Val Leu Ile Ala His Asn Gln Val Arg Gln Val Pro Leu
85 90 95

Gln Arg Leu Arg Ile Val Arg Gly Thr Gln Leu Phe Glu Asp Asn Tyr
100 105 110

Ala Leu Ala Val Leu Asp Asn Gly Asp Pro Leu Asn Asn Thr Thr Pro
115 120 125

Val Thr Gly Ala Ser Pro Gly Gly Leu Arg Glu Leu Gln Leu Arg Ser
130 135 140

Leu Thr Glu Ile Leu Lys Gly Gly Val Leu Ile Gln Arg Asn Pro Gln
145 150 155 160

Leu Cys Tyr Gln Asp Thr Ile Leu Trp Lys Asp Ile Phe His Lys Asn
165 170 175

Asn Gln Leu Ala Leu Thr Leu Ile Asp Thr Asn Arg Ser Arg Ala Cys
180 185 190

His Pro Cys Ser Pro Met Cys Lys Gly Ser Arg Cys Trp Gly Glu Ser
195 200 205

Ser Glu Asp Cys Gln Ser Leu Thr Arg Thr Val Cys Ala Gly Gly Cys
210 215 220

Ala Arg Cys Lys Gly Pro Leu Pro Thr Asp Cys Cys His Glu Gln Cys
225 230 235 240

Ala Ala Gly Cys Thr Gly Pro Lys His Ser Asp Cys Leu Ala Cys Leu
245 250 255

His Phe Asn His Ser Gly Ile Cys Glu Leu His Cys Pro Ala Leu Val
260 265 270

Thr Tyr Asn Thr Asp Thr Phe Glu Ser Met Pro Asn Pro Glu Gly Arg
275 280 285

Tyr Thr Phe Gly Ala Ser Cys Val Thr Ala Cys Pro Tyr Asn Tyr Leu

-continued

```
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Val Ser
                645                 650                 655

Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
    690                 695                 700

Ala Met Pro Asn Gln Ala Gln Met Arg Ile Leu Lys Glu Thr Glu Leu
705                 710                 715                 720
```

-continued

```
Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
    770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
    850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
    930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
        995                1000                1005

Leu Glu Asp Asp Asp Met Gly Asp Leu Val Asp Ala Glu Glu Tyr Leu
   1010                1015                1020

Val Pro Gln Gln Gly Phe Phe Cys Pro Asp Pro Ala Pro Gly Ala Gly
1025               1030                1035                1040

Gly Met Val His His Arg His Arg Ser Ser Ser Thr Arg Ser Gly Gly
               1045                1050                1055

Gly Asp Leu Thr Leu Gly Leu Glu Pro Ser Glu Glu Glu Ala Pro Arg
           1060                1065                1070

Ser Pro Leu Ala Pro Ser Glu Gly Ala Gly Ser Asp Val Phe Asp Gly
       1075                1080                1085

Asp Leu Gly Met Gly Ala Ala Lys Gly Leu Gln Ser Leu Pro Thr His
   1090                1095                1100

Asp Pro Ser Pro Leu Gln Arg Tyr Ser Glu Asp Pro Thr Val Pro Leu
1105               1110                1115                1120

Pro Ser Glu Thr Asp Gly Tyr Val Ala Pro Leu Thr Cys Ser Pro Gln
               1125                1130                1135
```

-continued

Pro Glu Tyr Val Asn Gln Pro Asp Val Arg Pro Gln Pro Pro Ser Pro
1140 1145 1150

Arg Glu Gly Pro Leu Pro Ala Ala Arg Pro Ala Gly Ala Thr Leu Glu
1155 1160 1165

Arg Ala Lys Thr Leu Ser Pro Gly Lys Asn Gly Val Val Lys Asp Val
1170 1175 1180

Phe Ala Phe Gly Gly Ala Val Glu Asn Pro Glu Tyr Leu Thr Pro Gln
1185 1190 1195 1200

Gly Gly Ala Ala Pro Gln Pro His Pro Pro Pro Ala Phe Ser Pro Ala
1205 1210 1215

Phe Asp Asn Leu Tyr Tyr Trp Asp Gln Asp Pro Pro Glu Arg Gly Ala
1220 1225 1230

Pro Pro Ser Thr Phe Lys Gly Thr Pro Thr Ala Glu Asn Pro Glu Tyr
1235 1240 1245

Leu Gly Leu Asp Val Pro Val
1250 1255

<210> SEQ ID NO 3
<211> LENGTH: 9
<212> TYPE: PRT
<213> ORGANISM: Homo sapiens

<400> SEQUENCE: 3

Phe Leu Tyr Tyr Gly Thr Thr Tyr Val
1 5

<210> SEQ ID NO 4
<211> LENGTH: 27
<212> TYPE: DNA
<213> ORGANISM: Homo sapiens

<400> SEQUENCE: 4
ttyytntayt ayggnacnac ntaygtn 27

<210> SEQ ID NO 5
<211> LENGTH: 9
<212> TYPE: PRT
<213> ORGANISM: Homo sapiens

<400> SEQUENCE: 5

Phe Leu Phe Thr Pro Thr Ile Tyr Val
1 5

<210> SEQ ID NO 6
<211> LENGTH: 27
<212> TYPE: DNA
<213> ORGANISM: Homo sapiens

<400> SEQUENCE: 6
ttyytnttya cnccnacnat htaygtn 27

<210> SEQ ID NO 7
<211> LENGTH: 9
<212> TYPE: PRT
<213> ORGANISM: Homo sapiens

<400> SEQUENCE: 7

Phe Leu Phe Asp Pro Thr Thr Tyr Val
1 5

<210> SEQ ID NO 8

-continued
```
<211> LENGTH: 27
<212> TYPE: DNA
<213> ORGANISM: Homo sapiens

<400> SEQUENCE: 8

ttyytnttyg ayccnacnac ntaygtn                                    27


<210> SEQ ID NO 9
<211> LENGTH: 9
<212> TYPE: PRT
<213> ORGANISM: Homo sapiens

<400> SEQUENCE: 9

Met Ala Gly Val Gly Ser Pro Tyr Val
1               5
```